US007176188B2

(12) United States Patent
Desnoyers

(10) Patent No.: US 7,176,188 B2
(45) Date of Patent: Feb. 13, 2007

(54) METHOD OF LETHALLY SENSITIZING HUMAN AND ANIMAL CELLS

(75) Inventor: Serge Desnoyers, Ste-Foy (CA)

(73) Assignee: UniversitéLaval, Québec (CA)

( * ) Notice: Subject to any disclaimer, the term of this patent is extended or adjusted under 35 U.S.C. 154(b) by 99 days.

(21) Appl. No.: 10/840,275

(22) Filed: May 7, 2004

(65) Prior Publication Data

US 2004/0265286 A1    Dec. 30, 2004

Related U.S. Application Data

(60) Provisional application No. 60/468,261, filed on May 7, 2003.

(51) Int. Cl.
*A01N 57/16*   (2006.01)
*C12Q 1/68*    (2006.01)
*A61K 38/00*   (2006.01)

(52) U.S. Cl. ............................... 514/44; 435/6; 514/12
(58) Field of Classification Search .................... None
See application file for complete search history.

(56) References Cited

U.S. PATENT DOCUMENTS

| 5,032,617 | A | 7/1991 | Lee et al. |
| 5,041,563 | A | 8/1991 | Fahrni et al. |
| 5,215,738 | A | 6/1993 | Lee et al. |
| 2003/0078212 | A1* | 4/2003 | Li et al. ................ 514/22 |

FOREIGN PATENT DOCUMENTS

| JP | 032-05402 A2 | 9/1991 |
| JP | 04-013684 A2 | 1/1992 |
| JP | 042-75223 A2 | 9/1992 |
| JP | 042-75296 A2 | 9/1992 |

OTHER PUBLICATIONS

Ying et al., "Poly(ADP-ribose)glycohydrolase inhibitor nobotanin B markedly decreases excitotoxic and oxidative neuronal and astrocyte death," Society for Neuroscience Abstracts, (2000) vol. 26, No. 1-2, pp. Abstract No. -88.15.*
Falsig et al., "Poly(ADP-ribose) glycohydrolase as a target for neuroprotective intervention: assessment of currently available pharmacological tools," European Journal of Pharmacology (2004), 497(1), 7-16.*
J. T. Slama et al., *Specific Inhibition of Poly(ADP-ribose) Glycohydrolase by Adenosine Diphosphate (Hydroxymethyl)pyrrolidinediol*, J. Med. Chem. 38 : 389-393 (1995).
J. T. Slama et al., *Mechanism of Inhibition of Poly(ADP-ribose) Glycohydrolase by Adenosine Diphosphate (Hydroxymethyl)pyrrolidinediol*, J. Med. Chem. 38 : 4332-4336 (1995).
H. Murata et al., *Characterization of Two Forms of Poly(ADP-ribose) Glycohydrolase in Guinea Pig Liver*, Biochemistry 30 : 5907-5912 (1991).
K. Aoki et al., *Novel inhibitors of poly(ADP-ribose) glycohydrolase*, Biochim Biophys. Acta 1158 :251-256 (1993).

K. Aoki et al., *A Macrocircular Ellagitannin, Oenothein B, Suppresses Mouse Mammary Tumor Gene Expression via Inhibition of Poly(ADP-ribose) Glycohydrolase*, Biochem. Biophys. Res. Comm. 210 :329-337 (1995).
Y.-J. Tsai et al., *Effects of Chemically defined Tannins on Poly (ADP-ribose) Glycohydrolase Activity*, Biochemistry Intl. 24 : 889-897 (1991).
Banasik et al., Specific Inhibitors of Poly (ADP-Ribose) Synthetase and Mono (ADP-Ribosyl)-Transferase, J. Biol. Chem. 267: 3, 1569-1575 (1992).
M. Banasik et al., *Inhibitors and activators of ADP-ribosylation reactions*, Molec. Cell. Biochem., 138 : 185-197 (1994).
F. Uchiumi et al., *Inhibitory Effect of Tannic Acid on Human Immunodeficiency Virus Promoter Activity Induced by 12-O-Tetra Decanoylphorbol-13-acetate in Jurket T-Cells*, Biochem. Biophys Res. Comm. 220 : 411-417 (1996).
J. Mao et al., *The inhibition of nitric oxide-activated poly(ADP-ribose) synthetase attenuates transsynaptic alteration of spinal cord dorsal horn neurons and neurophatic pain in the rat*, Pain 72 : 355-366 (1997).
M. Tavassoli et al., *Effect of DNA intercalators on poly(ADP-ribose) glycohydrolase activity*, Biochimica et Biophysica Acta 827 : 228-234 (1985).
L. Menard et al., *Rapid assay of poly(ADP-ribose) glycohydrolase*, Biochem. Cel. Biol. 65 : 668-673 (1987).
A. Gartner et al., *A Conserved Checkpoint Pathway Mediates DNA Damage-Induced Apoptosis and Cell Cycle Arrest in C. elegans*, Mol. Cell. 5 : 435-443 (2000).
D. W. Koh et al., *Identification of an Inhibitor Binding Site of Poly (ADP-ribose) Glycohydrolase*, Biochemistry 42, No. 17, 4855-4863 (2003).
W. Lin et al., *Isolation and Characterization of the cDNA Encoding Bovine Poly(ADP-ribose) Glycohydrolase*, J. Biol. Chem. 272 : 269-270 (1997).
Hammond, S. M. et al., *Post-transcriptional Gene Silencing by Double-Stranded RNA*, Nature, 2001, vol. 2, 110-119.
Collis, S. J. et al., *Enhanced Radiation and Chemotherapy-mediated Cell Killing of Human Cancer CElls by Small Inhibitory RNA Silencing of DNA Repair Factors*, 2003, Cancer Research, 63: 1550-1554.
Koh D.W. et al., 2005, "Extra Views: The Road to Survial Goes Through PARG", Cell Cycle, 4:3, 397-399, 2004.
Koh D.W. et al., 2004, "Failure to degrade poly(ADP-ribose) causes increased sensitivity to cytotoxicity and early embryonic lethality", PNAS, 51: 17699-17704 2005.

\* cited by examiner

*Primary Examiner*—Robert A. Wax
(74) *Attorney, Agent, or Firm*—Ogilvy Renault, LLP

(57) ABSTRACT

The present invention relates to a method, nucleic acid and amino acid sequences to sensitizing human or animal cells to be killed by chemical entities or irradiation. Particularly, the present invention describes nucleic acid and amino acid sequences pertaining to the group of PME factors, that are target to sensitizing the cells before treatment with killing elements.

7 Claims, 7 Drawing Sheets

B

PME-3  GGTTTAATTACCCAAGTTTGAGGCAGAAATAGACTTTCACAAAACACATCGACACTTCGAatg

PME-4  GGTTTTAACCCAGTTACTCAAGTTTTAGCAATTGAATTTTTAAATATAGTTTAACAACAACTGAAatg

C

A

B

...GGCTACGTACTTCTTAAGCA / TCAAACGTAAGCTCGATGGA...

1382 ⟋   ⟍ 3687

C

SEQUENCE LISTING

<160> NUMBER OF SEQ ID NOS: 29

<210> SEQ ID NO 1
<211> LENGTH: 3009
<212> TYPE: DNA
<213> ORGANISM: Artificial Sequence
<220> FEATURE:
<221> NAME/KEY: CDS
<222> LOCATION: (1)...(3009)
<223> OTHER INFORMATION: pme-1

<400> SEQUENCE: 1

```
ggtttaatta cccaagtttg agattgtcat acgggtcccg gatgattcat tccaacgagc      60
cactgcccta cgctatcgaa tatgcaaagt ctggccggtc gaattgtaaa acatgcaaaa     120
agaatatcgc gttggatcaa ttgagaatgt caatgaatcg cccgtcaaca ttcttcgatg     180
gaaacatgga ttcgtggttt cactacaatt gcttctggat aaaaatgatt cgcggccgag     240
atgacatcaa tataagctca atccgaggag tcgattggct tcgctgggaa gatcaggaaa     300
agcttcgcca ggaaattcaa cactttaaaa ccgcatcgcc accgactctg acacccctgt     360
gctctaccac taccgtcatt ttgtccacaa taaaaaccga aaaatcgttg tcaaatcgtg     420
ggaaatgtgg aaaatgcggc caaaatttcg agcgcggcga atcaaggct cataacaagg      480
gaaaagccaa ccatttgaat tgttttctgc aggaatttga taaaatttcc ggcaccgttg     540
aggatattcc tggctgggcg gattatgagg agaactttaa aattaaggcg ttggggagt      600
atgtggaggc tttagctgcg aaaaggcgat ccacggagcc agctacccg gcttctgcct       660
ctccaacacc accagaagct gaaactccag ttttatctgc agaaggatcc ccggaaagct     720
ccaataaacg tccggcaagc tctgaaatca ttgaaatcga cggtgaaggg aatccagatg     780
agaatgattt tgcgaagaaa agacgaatga agaaggaagc cagattgatg gaggttcaga     840
agaagcgaat gaagaaacaa tccgatcttc tctgggaata ccgccagatc ttcgaaagaa     900
tgccgtacac cgacaaaatc tctatattac gagaaaacga gcaagacatt ccagaaggac     960
acgatccgac tgcacaagta atcgaacgcc tagtggataa tgccctattc ggatgcccaa    1020
tcatttgcca acatgttcaa atggaaaaaa ttgtctataa ttcatcatgc cgcacatatg    1080
tctgcactgg atatgctaca gaatactcga atgtactta tgaatcaaag aatccaattc      1140
gaactccatt cgaagtttct caccgattaa ctgaaaagca taagcttcaa gatattgtat    1200
tcaatcaaat gagtgaacga ctttatatag gagaagagga tggagaatct gtagtgaaaa    1260
ttgataaaag aaagtcgaaa ggtggtactc gtggtgaaca attcatttat gcggctgaag    1320
cattcgattc gactaacaat gttccgataa agtcggcga tctcacatca accaatactc      1380
atattattaa aaaggaaca gttgttgatg cgaaattcgc actggccgat cgttgtcatg      1440
tattcaaaaa tgagattgat ggaagtctct atcaggcgac actctcgttt actgatctta    1500
cacagaataa gaattcgtat tataagattc aactgttgaa ggatgatcag agagaaaact    1560
actacgtctt ccgttcttgg ggtcgagttg cacagaagt cggcggaaat aagcatgaat      1620
catacagtaa ttcaaatgaa gcgattctca aattccagga tgttttccac gaaaaaacga    1680
agaacgattg gatttataga aaacatttcc gcaaatgcc cggaatgttc agctacgtgg      1740
agacggatta ctcggaattt gcacaaataa cggacacaga aatcactcca ggatcaaaaa    1800
ctctacttcc aaaatctgta aaagaagttg taatgtcaat tttcgacgtt gaaaacatga    1860
aatctgcatt aaaatcgttt gaaatggatg tgaataaaat gccgcttgga agattatcac    1920
```

-continued

```
ataatcaaat caatttggct tttgaagttc tcaatgatat tagtgatttg cttgtcaagc    1980
tgcccattga tgcttcgaga atttttggatt ttagtaacaa gttctacacg attattccgc   2040
ataattttgg aatgcgggtg cccgagccga ttgatagttt tcataaaatt aaggagaaaa    2100
acaacatgct caacgcccct ctcgacatca aattcgcgta tgatcaaatc agcggtggag    2160
atgttccagc atcaacgtca ttgggtattg atccagttga tattaattat caaaaattga    2220
aatgtattat ggaaccacta caacaaggct gtgatgattg aatatgattt catcaatatt    2280
tgaagaatac tcacggagcc actcatgatt tgaaagtcga gctgattgat attctaaaac    2340
tgaaccgaga caatgaatcg tcgaaattca acgacacat cggaaatcga cgtcttttgt     2400
ggcacggatc aggaaaaatg aatttcgccg aattttgggg tcaaggactt cgaattgcgc    2460
caccggaggc tccagtttct ggatatatgt tcggaaaggg cgtctatttt gctgatatgt    2520
tcagcaaaag tttcttctat tgcagggcca acgccaaaga agaagcatat cttctgctct    2580
gtgacgtggc actcggcaac gtgcaacagt tgatggcttc gaagaatgtt tcgagacaaa    2640
ctctgccagc aggcttccag tctgtgcagg gactaggccg ccaatgtcca cgagaaattg    2700
gaagttacaa tcatccggat ggttatacca ttccactggg cctcacttac atgcaacttc    2760
aaggaaaaca ggatgtcgat tatcacttgc tttataatga attcattgtg tatgatgtcg    2820
atcaaattca gctcaagtat ctcgtccgtg tcaaaatgca ccatgctcgt catctttaac    2880
aatttaatct tattgcctgt ctcgccccc acccccaata cctcgtgcct ttagctgata     2940
ttctatttga tcccccactc tctctaaaaa aagaacatc gagtgccata tgaaattta     3000
tttttgttc                                                           3009
```

<210> SEQ ID NO 2
<211> LENGTH: 1902
<212> TYPE: DNA
<213> ORGANISM: Artificial Sequence
<220> FEATURE:
<221> NAME/KEY: CDS
<222> LOCATION: (1)...(1902)
<223> OTHER INFORMATION: pme-2

<400> SEQUENCE: 2

```
ggttttaacc cagttactca agctagacag aaatgtctat aatcaacgac gaaaatggaa    60
gaggctataa agtacatctt tgcaagacga atattgcaca gaacaacaat aaattttacg    120
atatggaatt gttggatgag ggaggtgatt tcattgtgaa gcttatcaat ggacgtattg    180
gatatcgtgg tgtcacacaa ttaaaagatt tcgatgacct cgacagagcc aagaagttct    240
tcgaaagcaa attctacgag aaaactcatc ttcattggga agaaagagac gatgaaccgg    300
ttcccaataa atatgcagtc gttgagttgg ctactaacgc aagacagact gaaaaagaag    360
ttaaaaagga ggaaccggaa cctgagccga agttgatga gaaaaataca cgtggaagga    420
agaaaagagg aattgttaaa gaaaagaaag aaatcaagaa agaagaggaa ccagttgaag    480
aagttaatga aaagctgaag gaattgatga aatgcatctg cgacgaagat gttcatctgg    540
gactcttgaa acaactgaaa tttaacgaag cttttggaag accaattgat tgcctctcac    600
ttgcccaact caccactgga tatgaaattt tgagtaagat tgaggaatcg attggaggaa    660
aatcagctcg aagatctact cgtggccggc cacgagtagc tgaccgtgtt cttgctgtta    720
aatccgatgg tccatctctt cacgacatca acaaatatta ttctctcatc cctcattcat    780
ttggtttctg tgttcctcca aaaattgatt ctcatgctaa aattcaagct gaacgagagc    840
```

-continued

| | |
|---|---|
| ttctggatgc actgaaagga tcaattgaag catcactgga actgaaggat ttgaaaaaga | 900 |
| cagcatcgtc gaaggatatt tatcaaagac tttatgagcg cctcccgtgc catttggagc | 960 |
| cagtttcgga agaaattgca ggaaaaattg gagactgctt ggctatgcgt ggacccactc | 020 |
| attgttacaa gctttcactc attgatgcat tcgagttaaa ggatccaaat gaaattccaa | 080 |
| ctgaagctcc agttgaagtt caggaagttc gaagaagag aggacgaaag agcacaaaga | 140 |
| ccgctgctcc aactgttcca ccaccaacta caaaacgcct tctttggcac ggtactcgtg | 200 |
| tgacaaatgt cttctcaatc ctcatgaatg gacttcagtt cccagttgga gatcgctgtg | 260 |
| gtctgatgtt cggaaatgga gtttatttcg caaatgttcc aactaaatcc gcgaattact | 320 |
| gttgcccaga ggcttcaaag agagttttca tgcttctttg cgaggttgaa actgcgaacc | 380 |
| cattagttct ctacgagtca gaaattgacg cggatgagaa aatggaaaaa gcgaaaaaga | 440 |
| cgtcggttta tgcagctgga agcacactc aagagacac tgttgaaatc aatggaatcc | 500 |
| cggcattcaa gtcaaatctt gagacaatcg aagaagaaac tcgtcttctc tacgatgaat | 560 |
| atgtgatgtt caacaaggaa cacttcaaaa taaaatatgt tgtcgaagtg aaagtggatc | 620 |
| gtcttaccgc taaggaaatg atggcttaaa tgctaatttc tcatgtaatc tctcacagtt | 680 |
| tatctgtttc tacctctcca tttaattttc tgatctgaat ttgtcaagct tttgtaactt | 740 |
| tttttaaacc tgttaatcca atgatactcc tcattttttt aaaatcacat tcctggaatt | 800 |
| tgttttgct caaaatctca tcttttcgg tttcacttca ttcattttct gctcatatca | 860 |
| aaaaacaaat gtattttga agcaaaaaaa aaaaaaaaa aa | 902 |

<210> SEQ ID NO 3
<211> LENGTH: 2666
<212> TYPE: DNA
<213> ORGANISM: Artificial Sequence
<220> FEATURE:
<221> NAME/KEY: CDS
<222> LOCATION: (1)...(2666)
<223> OTHER INFORMATION: pme-3L

<400> SEQUENCE: 3

| | |
|---|---|
| ggtttaatta cccaagtttg aggcagaaat agactttcac aaaacacatc gacacttcga | 60 |
| atgagcaaga agtttatcga actgggtgat cctgtcactc aagacgagaa agactacgaa | 120 |
| gactatgtcg gagttggttt cgcgcatcaa gtcccgacaa tgaaaaggcg aagttgaca | 180 |
| gaacatggaa atactacaga atcaaaagaa gatcctgaag agccaaaaag ccgtgacgta | 240 |
| tttgtctcct cgcagtcaag tgatgagagt caagaagatt cggctgaaaa tccggagatc | 300 |
| gctaaagaag tgtcagaaaa ttgtgaaaat ctgacagaaa ctctcaaaat ttctaatatt | 360 |
| gagagtttgg acaatgttac tgaaagatct gaacacactc ttgataatca caaagtact | 420 |
| gaaccaatgg aagaagatgt aaacaacaag tccaatattg acgttgcgat taattctgac | 480 |
| gaggatgatg aacttgttct ggaagagaat aataagaaa tgagggatgg agaacaagta | 540 |
| caacaggatt tattcgctga tgatcaagag ctaattgaat atccaggaat tatgaaagac | 600 |
| actacaactc aactggatat aacagattct gaagtggaga ctgctcaaaa aatggaaatg | 660 |
| attgaagaaa ctgaagcaga ttcgacattt gtaggcgagg attcaaaaaa tcagcggcaa | 720 |
| agtggcacta ctagtgacga agttgacgca gattctcaga ttaatttggc tacgaaaact | 780 |
| gtgaggacat ccagttcaag tttcctgtca actgtttcaa catgcgaagc ccctgcaaaa | 840 |
| ggacgagcaa gaatgtatca aaaagagttg gaaaagcatg tgattgcatt tactgaggga | 900 |
| aatctcacac tacaaccaga tttgaacaaa gttgatcccg acagaaacta tcgatattgt | 960 |

―continued

| | |
|---|---|
| acaattccga actttccagc ttcccaagga aaacttcgag aagataatcg atatggccca | 1020 |
| aaaatcgttt tgcctcaaag atggcgagaa tttgattcga ggggccgtag aagagactca | 1080 |
| tatttctatt tcaaacgtaa gctcgatgga tatttgaaat gctacaaaac aactggatat | 1140 |
| tttatgtttg ttggactttt gcacaacatg tgggaatttg acccagacat cacatataaa | 1200 |
| ctgccagcac tggaaatgta ttacaaagag atgtcggaac ttgttggtag agaagaggtt | 1260 |
| ttggaaaaat ttgcacgagt tgcccgcatc gcaaaaactg ctgaagatat tctgccagag | 1320 |
| cgaatttatc gtcttgttgg tgacgtcgaa tcagctacct tgagccacaa gcaatgtgct | 1380 |
| gcacttgttg cgagaatgtt ttttgcccga ccggacagtc ctttcagttt ctgccgaatt | 1440 |
| ctctcgtctg ataaatctat ttgtgtggag aaacttaaat tcctgttcac ttatttcgac | 1500 |
| aaaatgtcaa tggatccacc ggatggtgcc gtcagtttta gacttacaaa aatggataaa | 1560 |
| gatacgttca acgaagagtg gaaagataaa aaattacgtt ctcttcctga gttgaattc | 1620 |
| tttgatgaaa tgcttattga agacacagct ctctgtacac aagttgattt tgcgaacgaa | 1680 |
| catcttggtg gcggagtttt aaatcatggg tctgttcagg aggagatccg tttcttgatg | 1740 |
| tgtccagaaa tgatggttgg aatgttgttg tgcgagaaaa tgaaacaact ggaagcgatt | 1800 |
| tcaattgttg gagcttacgt tttcagttct tatactggtt atggtcatac tctaaaatgg | 1860 |
| gcagaacttc aaccaaatca ttctcgtcag aatacaaacg aatttcgaga tcgttttgga | 1920 |
| cgtcttcggg tagaaactat tgcaatcgat gcaattctgt tcaaaggatc aaaattagat | 1980 |
| tgtcagacgg agcagttaaa caaagcaaat atcattaggg aaatgaagaa agcatctatc | 2040 |
| ggattcatga gccagggacc gaaattcaca aatattccaa ttgttactgg atggtgggga | 2100 |
| tgtggagcat ttaatgggga caagccactg aagttcataa tccaagtaat tgctgccgga | 2160 |
| gtcgctgatc gtccacttca tttctgttca tttggagaac ccgagcttgc cgcaaagtgc | 2220 |
| aagaaaatta tagaacgaat gaaacagaag gacgtaacac ttggcatgct attcagtatg | 2280 |
| ataaacaaca ccggcttgcc acataagcac tttgaattct acgtcttcga tagaatttct | 2340 |
| acttatctca gtagttcgga agatgttgag tcttcgaaat catcaccttc agtatcccga | 2400 |
| gcataattcg aatcgcccac acggccataa agaccggttc ctttcgatta aattctgtta | 2460 |
| aatatgcatg ctccgtcttt aaaaaatcag tccccgtatt ttaaacgttt tgattttaat | 2520 |
| gttcatatta ttatccgaaa ttagtatact cgccgtcatg aaagcccgag atatctagtt | 2580 |
| cgcaagtcag aaattttcg gagcatcgtc gtgatatatg aataaataca ttcctgttta | 2640 |
| aaaacaaaaa aaaaaaaaa aaaaaa | 2666 |

```
<210> SEQ ID NO 4
<211> LENGTH: 2615
<212> TYPE: DNA
<213> ORGANISM: Artificial Sequence
<220> FEATURE:
<221> NAME/KEY: CDS
<222> LOCATION: (1)...(2615)
<223> OTHER INFORMATION: pme-3S

<400> SEQUENCE: 4
```

| | |
|---|---|
| ggtttaatta cccaagtttg aggcagaaat agactttcac aaaacacatc gacacttcga | 60 |
| atgagcaaga agtttatcga actgggtgat cctgtcactc aagacgagaa agactacgaa | 120 |
| gactatgtcg gagttggttt cgcgcatcaa gtcccgacaa tgaaaaggcg gaagttgaca | 180 |
| gaacatggaa atactacaga atcaaaagaa gatcctgaag agccaaaaag ccgtgacgta | 240 |

| | |
|---|---|
| tttgtctcct cgcagtcaag tgatgagagt caagaagatt cggctgaaaa tccggagatc | 300 |
| gctaaagaag tgtcagaaaa ttgtgaaaat ctgacagaaa ctctcaaaat ttctaatatt | 360 |
| gagagtttgg acaatgttac tgaaagatct gaacacactc ttgataatca caaaagtact | 420 |
| gaaccaatgg aagaagatgt aaacaacaag tccaatattg acgttgcgat taattctgac | 480 |
| gaggatgatg aacttgttct ggaagagaat aataaagaaa tgagggatgg agaacaagta | 540 |
| caacagttgt cacaggattt attcgctgat gatcaagagc taattgaata tccaggaatt | 600 |
| atgaaagaca ctacaactca actggatata acagattctg aagtggagac tgctcaaaaa | 660 |
| atggaaatga ttgaagaaac tgaagcagat tcgacatttg taggcgagga ttcaaaagct | 720 |
| acgaaaactg tgaggacatc cagttcaagt ttcctgtcaa ctgtttcaac atgcgaagcc | 780 |
| cctgcaaaag gacgagcaag aatgtatcaa aaagagttgg aaaagcatgt gattgcattt | 840 |
| actgagggaa atctcacact acaaccagat tgaacaaag ttgatcccga cagaaactat | 900 |
| cgatattgta caattccgaa cttccagct tcccaaggaa aacttcgaga agataatcga | 960 |
| tatggcccaa aaatcgtttt gcctcaaaga tggcgagaat ttgattcgag gggccgtaga | 1020 |
| agagactcat atttctattt caaacgtaag ctcgatggat atttgaaatg ctacaaaaca | 1080 |
| actggatatt ttatgtttgt tggactttg cacaacatgt gggaatttga cccagacatc | 1140 |
| acatataaac tgccagcact ggaaatgtat acaaagaga tgtcggaact tgttggtaga | 1200 |
| gaagaggttt tggaaaaatt tgcacgagtt gcccgcatcg caaaaactgc tgaagatatt | 1260 |
| ctgccagagc gaatttatcg tcttgttggt gacgtcgaat cagctacctt gagccacaag | 1320 |
| caatgtgctg cacttgttgc gagaatgttt tttgcccgac cggacagtcc tttcagtttc | 1380 |
| tgccgaattc tctcgtctga taaatctatt tgtgtggaga aacttaaatt cctgttcact | 1440 |
| tatttcgaca aaatgtcaat ggatccaccg gatggtgccg tcagttttag acttacaaaa | 1500 |
| atggataaag atacgttcaa cgaagagtgg aaagataaaa aattacgttc tcttcctgaa | 1560 |
| gttgaattct ttgatgaaat gcttattgaa gacacagctc tctgtacaca agttgatttt | 1620 |
| gcgaacgaac atcttggtgg cggagtttta aatcatgggt ctgttcagga ggagatccgt | 1680 |
| ttcttgatgt gtccagaaat gatggttgga atgttgttgt gcgagaaaat gaaacaactg | 1740 |
| gaagcgattt caattgttgg agcttacgtt ttcagttctt atactggtta tggtcatact | 1800 |
| ctaaaatggg cagaacttca accaaatcat tctcgtcaga atacaaacga atttcgagat | 1860 |
| cgttttggac gtcttcgggt agaaactatt gcaatcgatg caattctgtt caaaggatca | 1920 |
| aaattagatt gtcagacgga gcagttaaac aaagcaaata tcattaggga aatgaagaaa | 1980 |
| gcatctatcg gattcatgag ccagggaccg aaattcacaa atattccaat tgttactgga | 2040 |
| tggtggggat gtggagcatt taatggggac aagccactga agttcataat ccaagtaatt | 2100 |
| gctgccggag tcgctgatcg tccacttcat ttctgttcat ttggagaacc cgagcttgcc | 2160 |
| gcaaagtgca agaaaattat agaacgaatg aaacagaagg acgtaacact tggcatgcta | 2220 |
| ttcagtatga taaacaacac cggcttgcca cataagcact ttgaattcta cgtcttcgat | 2280 |
| agaatttcta cttatctcag tagttcggaa gatgttgagt cttcgaaatc atcaccttca | 2340 |
| gtatcccgag cataattcga atcgcccaca cggccataaa gaccggttcc tttcgattaa | 2400 |
| attctgttaa atatgcatgc tccgtctta aaaaatcagt ccccgtattt taaacgttt | 2460 |
| gattttaatg ttcatattat tatccgaaat tagtatactc gccgtcatga aagcccgaga | 2520 |
| tatctagttc gcaagtcaga aattttcgg agcatcgtcg tgatatatga ataaatacat | 2580 |
| tcctgtttaa aaacaaaaaa aaaaaaaaaa aaaaa | 2615 |

<210> SEQ ID NO 5
<211> LENGTH: 1558
<212> TYPE: DNA
<213> ORGANISM: Artificial Sequence
<220> FEATURE:
<221> NAME/KEY: CDS
<222> LOCATION: (1)...(1558)
<223> OTHER INFORMATION: pme-4

<400> SEQUENCE: 5

```
ggttttaacc cagttactca agttttagca attgaattttt taaatatagt ttaacaacaa      60
ctgaaatgga tcatgaaaac ttaatgaagt atttggaaga attcagaagc atcagatttc     120
aaccagattt ccaaaaagtt gatgctgaaa ggaatgttag atactgtgaa attacggatt     180
ttcctatttc taacatatcg tttgagctac tggaaacagg ggtgtctcaa caatggagaa     240
attgtgatca aaatttgttc aatgaatatt tgaaaactta caaaaatgga ggatattcgc     300
agttcgagga tcttcttttc aaaatatggg gatattctga agaaaagaa agatttgatt      360
taccagcact aaagtcgttt taccgcaaaa tgtcagaaat tgttggagag atgaagttc      420
ttgaaaaatt agcaagatta gttcgaatta ccaaatcagc ttgtgaagtt cttccagaga     480
aaatttatcg gcttgtcgga gatattgaat cagcaacttt cagtcatatt caatgtgcat     540
cactaattgc ttggatgttt ttcagtgaca cacctcgatt gagtttcatt ataattcttc     600
aaaaaacgac ttgtgtcgca gtggaaaaac tgaatttttt gttcacatac tttgataaaa     660
tgtcaataga tcctccaatt ggtgctgtca gttttcgtaa aatgagaata acacataaac     720
aatatttgga aaattggaaa ttaagagaaa ctaatttgtt gccagatgtt caagtatttg     780
ataaaatgtc cattgaggag accgcactct gcacacaaat cgattttgca ataaacgtc      840
tcggaggcgg agttttgaaa ggaggagctg ttcaggaaga aattcgtttt atgatgtgcc     900
ctgaaatgat ggttgctata ttattgaatg atgtaactca agatttggaa gctatttcaa     960
ttgttggagc ctatgttttc agttcctata ctggatattc taacactctc aaatgggcca    1020
agataacacc aaagcactct gctcaaaata acaattcatt tcgggatcaa tttggacgtc    1080
ttcaaactga acagttgca attgatgctg ttcgaaatgc ggggacgccg ttggaatgcc     1140
ttttaaatca attaacaact gaaaaattaa cacgagaagt tcgaaaagct gcaattggat    1200
ttttgagtgc cggtgacgga ttttcaaaaa ttccagttgt atcgggatgg tggggatgtg    1260
gagcatttcg aggaaataaa ccattaaaat tcctaattca agtaattgct tgtggaatttt   1320
ctgatcgacc actacaattt tgcacattcg gagacactga actggcaaaa aagtgcgaag    1380
aaatgatgac gttattcaga aataacaatg tcagaacagg ccaactatttt ttaattatta   1440
attccatcgg gccaccactc aactattctg aacagtatgt ttttgatgca atcagagcaa    1500
aaatcaattc caccaaagca tgaaaaaaaa aaaaaaaaa aaaaaaaaaa aaaaaaaa       1558
```

<210> SEQ ID NO 6
<211> LENGTH: 6885
<212> TYPE: DNA
<213> ORGANISM: Artificial Sequence
<220> FEATURE:
<221> NAME/KEY: CDS
<222> LOCATION: (1)...(6885)
<223> OTHER INFORMATION: pme-5

<400> SEQUENCE: 6

```
ggtttaatta cccaagtttg agccgtaatc cgaacagcat ggctcgtcgt gttaataaga      60
```

-continued

```
aaaagtctcc tgtaaaagct gccaggaaaa ttgatgggca aatcgggaga cgagttgtgg    120
acggagtccg tgccaagtcg tcccgtcaac gccatcaagc agttctctac caggctccca    180
ctcccactgt gattcgccgt aagaccacga aaacggcgat cgtcaagaaa acagttgtag    240
ttgtgaaaaa gggtggaaaa gttgtcaaga atcctctaa aactggtcag aaagtgaaag    300
cagtgaaggc gccaaaagtc aaagcaccat ccaagaaggg aaatgatcga cttactccac    360
gtgtcatcac tgagtaccag gagaatccgt ttttctacga tcctcaggtt ccagagtaca    420
tcagtgcctc cgtctaccac agatggatca ccagagccgt tcgcaatgga aatatgaagg    480
aaatcaaaga ctattataag tcgaagaagt gccaaaaatc tgcaatctac acgagctttg    540
cctatagttt cgacacttcg gcgtgtgatg aagcattgag gcaggacatc aaatttgcca    600
ccgagttctt caaaatgaac aataaaatgg aagttgataa ttcctatcat ccgggcaaag    660
agccgaatct gttgcaaaag aaaaccaccg tcgcaagaa ctactacatg ctcggccgcc    720
acacgcgcca gattgagatg ggaagaggtg gcaaagaagg aaacaatgct cttttgaact    780
atgacacaag gaccgatgag ccaaatccat tgacgaagct tatcgaggat aatgtgacat    840
acactaagtt gtatcaactt tgcaagattc cagacggacc gattgtcgaa catcacatcg    900
aaatgcactt cgtcactgct gttcgaatgg gccaccgcga tcttgcatcc gcgttggcac    960
agggacccgt caaatgcac tgcaacgatc ttcaccgtgc aactctgaaa gatcagaaac    1020
tgcccgccaa aatccttcca gtatctgttg cgaaaaaggc gtacatgaat aagaatatca    1080
ctccacttca cactgccgcc atttccaact ccacccatat gctagaagcg atgagagccg    1140
tctacccaac gatcaacatt ccggatcaag acaactggta tacgatgcac tatgccgcgt    1200
gtgctcctgg aactgctcct atggaatttc ttctcaaaaa cggtggatct gttacgatgc    1260
tcaccaagca aaccgaaacc ccactgcatg tggctgccag agctggaaga gctgtgaatt    1320
gcacattttt tgatgaaggaa atgctggatt tggagaaagg agacgacgga gagagcacaa    1380
tcagagctga cagatctatc atcaatgcga gaactcgctc tggaaactct gcacttcatt    1440
tggcggtgct acgtaataac cttgacgttg ttgatgcctt gctcgccgag ccaaccatcg    1500
ttgtagacaa tccaacatcc acaggacaaa acagattaac tccattgatg atggcatgtg    1560
gaaaaggata cctagagatg gcgaagaagt tggttgagaa gggagcattg gtggaaggaa    1620
aagataagaa aaagcgtacc ccgttaatcc acgcaatgct caatggtcag attcacactg    1680
cagccttcct cctcgccaag ggagctagtc ttactctcgc ggattcgtct ggaaatactg    1740
ctgctcacta cgctgctgca tatggatttt tggactgctt aaagcttctt gcctcaattg    1800
atgataatat tctatccgag ccaaatgact ggcagcttta tccattgtcc gttgcatatc    1860
tcaaaggtca ttatggaatt gttacgtggc tcctggaagg tccgcacaag gataaagcta    1920
acattaatgc aaaggacaac aacggtgcaa ctcttctctc gaatttgctc tcatatgctg    1980
acgagacaat gcataaagaa ttgctaagtc aaattgaata tctggttgca agaaaagccg    2040
atgcatcact tgctgacagc tctgggcaaa ctccactgca cctgttctcc atgcaacgga    2100
tcattctgaa aggttctgga gaagccgctg agaacgatgc aatgagaatg actttggaca    2160
actacaaaaa gtgcttcaat acactgatca aagccggagc caaagttgat gtctatgatc    2220
atgaggacaa tacaccatta cattatgcac tcaccaacgg aaacttgatg ctcttcaatc    2280
tgatgctgga taaggttgca aataagagaa atctttttga gaaatgggca aaccaccaaa    2340
acttcctgca cgagatcctt gctcttccaa tgaaagttta cggagatcaa gttttgtgga    2400
agggagagac gctcaccaaa ccagcatatg atgttcttcc gattcttaag gagttacacg    2460
```

```
agaacttgcc ggatttattt gagaaatgga tcagtgaagt gaataaagct gggtactcgc    2520
cgattgtgga agctatcaag caatatcaag ctctggcggc aaacaaaaag cttcgtggag    2580
aagctgatca gacattcatc tcgaccgtca acgagctttt cgaatgggtg attcgccttg    2640
gaccgttcca gctgacgcaa aaatacatta attctgagaa ctctgcagct gtcacactgg    2700
ccaatcttgc catgagcatt ccgatcgagt gtggaaggca tcaacagaat cagttggcac    2760
tattcaaaat tctcatcaaa ttgagcaagg agttcaacaa ggtcgatgag ttttttaacgc   2820 agaaaaacga gaaagacgat gttctgatcg tacaagcgat catgtttgac aagccaaatg    2880
tggtagagct catcctggac accgcctcag aaatgcacct gatccacgga actcacaatg    2940
caatcaagga gaacgagtta gaagttgtag ttcacaagac aatcatcatg tacatgattg    3000
agatgagaat gtgggagctg ataccgaagg tgaatgcatc gagcgagttc tggaagagca    3060
aggacgccaa gggtaatagt gtctggcact atgctgcacg agttaacagt cataaaactg    3120
ttgggctttt caaaatgatt gagtcgaagg gtgttcggag agaaacaaat gacgatggac    3180
gctctgttct ccacgtggca actctggctt gtgatggatc cgccgattct gtgctggagc    3240
cgattgcttg gctatcaact cgttgtccaa ttgatgcggt ggataagttc aatcgaactg    3300
ctcttcacta cgcgttcgga aacgaaaatg acttcaaaga aggcaatgtt ccgtttggtg    3360
agagtgatcc gattgcagta gtttcacttt tgtcatctct gattcgacca gaacaaattg    3420
aaattgccga tgttaatgga aatacgattc ttcatcttgc tgcaatcaag aattctacta    3480
tttgcctgat gactctgatt cgaaagaaat gccacgtaga tttgaagaat aaggatggaa    3540
acactccact tgctcttgct gttcatcatg gaagacaatc atccgctttg actttgattc    3600
aagctaacgc agatgtcact gaaaagattt tcgtacctgc tctgaagcca acgtccgatt    3660
tcgaccaaaa cagtagcggc acggaagctg agaaattctg gaagtggcat ggaaaagaga    3720
aaaaagtttt ggaggatctg cacacaacga ttccagcgtc ggtggtgagc aagggtggaa    3780
gttgggaagc aatggtctac gttttactgg acgttctcgg acaaaacact ggaagtatgg    3840
cacagctcac tgatgcagca ttgcgacgtg gacaactcaa tcttgccaat cagctgctca    3900
agtccataga agcgttgatt gatggagcag ttttgaatag ctcttatgat ctgttggata    3960
catttgctga gaaatgtttt ggagcattaa cctcggaaga aactatcgag aagacagttt    4020
tgaatagaat tattctcact cgcggccttg gcttgaagca accagaaact atgaaaatta    4080
tcaggacggc tctgcagaat ggaaactgga atttgctcaa cttttttgaag tctgaaatgg    4140 gaacagcttg gaagaaccag aaaatcgaga caccaactga aaatccaatc cgatcacttc    4200
tcatatacat gaacgaaaaa tcagtcagct cggaggcaat tggattcctc gaagagctca    4260
gacagatgcg aggtgtgaac attgacgctt tgtgccagtt ggaaattccc ggaaaattca    4320
aaaagatttt ggattatgga ctcattccgc caatctcatt tgctgttctc caagaaaatc    4380
caaatatgat cagagctctg agaaatgccg gtgcaagtct caaaactcaa gacgactatg    4440
gcaggacccc gctgatgtat gcaattatga ccaacaaccg ctccgtcgtt gatgcaatcg    4500
taggtgacgg taaactagct gtggtgcttc ataagcagaa ggcagtggca accgggccaa    4560
gatgcgtagc agttccgatg cggttttggag caactagccg ggcttttatt cctgcggctg    4620
catttgcttc tgttcccgct agagtcgaat ctgatgaaga agaagaggat aactctggtt    4680
cggaatcagg agaagatgga gcagcctctg aaaataaatc tgaacatggc tcagaaaatg    4740
gcgaatctgg caatggttct gacgacgagg acgacgacga tgatgattct tctccaccac    4800
```

```
ctgccaaaaa gtctcgaatt gcaaaagagg ctgctggacc atcaacagga cctaagcgaa    4860
agaaacttgt cattactgat ccatcgctct tctcggcacg cgatcacaaa gagaacaacc    4920
ctcttcatta cttcattgag ccgctcgcct gggagaatgt ggaacttctt ggagatttgg    4980
ctgcagccaa caagaccgct attgtacaat gtctgattga taagagaagt ccgaatccga    5040
ttgagttggc cgcgatgaaa atgaatcgaa gaatgaaaag cgaaatgctc aaaattgtaa    5100
agaatgctgc attcccacga cccattaagg aaacaaagct cactcttcaa caagtacaca    5160
ttgaaccatt gagtgatgta gatgaagatg ctgcaaagtt cctcgcaaaa tgggttgaag    5220
agaaggacaa gaaaaagact agcgaggcac aaaaccgca caaaagctca acctattcga    5280
ccaatgggct cgtcagcttc tgcgacgaaa ctcaacagta ctttgatgtg ctcatgaaca    5340
agactgattt gatgtatgga agatgtggat tccacaattt ctatcgcatg caaatcatca    5400
aacgacgtga cgctgagttg ttcatcttgt tcacgaattg gggacgaatt ggatcgggaa    5460
tgggcgagtt tcagaccacc ccattcaaca gtcttgagtt ggcagccaaa gaattcaagt    5520
cgatcttcaa atcaaaatct ggaaatgaat gggctccact tgccaacttc cgagatatgc    5580
caaagaagta taggcttgtt gaaaccgatt ccacaccgac tagtctggct gaaatcgaac    5640
tgacgtggaa aaagaacacg gagaaggatc cgattcgtag aatgattgct gatattagcg    5700
atgcgaagac tctgaaaacc tatgcctctc aagttcaaat gtacggagga agtagccaac    5760
cattcggacg attcaccaag gagaatattg aaaaggcaaa gttggtattg acaagttgg    5820
agaaaaatgc aaatagaatc aagcagatgg tcgaggcgca gactggagtc gtggagtcca    5880
acttgctaga tgcatatatt actactagcg agttatccgg agactattac agtctgatcc    5940
catccggcga atatgagttc agtaacctca cccgtcttga caacgtcgag gagattgccc    6000
gccaccgtgc ccgtctgaac cgatgccagg aaattgaaac tgccaccgt ctgctctgcg    6060
cggcagagtt ccgtcaagat ttggatcgag tcgactatat cagaagtgcg attcaatgcg    6120
aataccgact agaaactcca gactcggata tcagtcagcg ccttcttcaa tggatccata    6180
atagtggtgg aaagcaagca aaggttaaga tgattctgga aatttcgcca atgctatcaa    6240
ctgaaaaatt cgagccattt gtgaacgatg ataatcaaaa gttcttgtgg cacggaacaa    6300
aggcgacgaa tttgatgagc attttgaaga atggattcct catcgaccca ccaagtgcat    6360
gcaaaaatgg aaacctgttc ggttctggaa tctacttggc agacagcttt gaaaaaagca    6420
cacactactg ccagccatca gcgggtggca tcaactatat gctcgtctgc cagacagctc    6480
tcggaaaagt cagaactctg gacacgattc cctatcacta catgaatcaa tcaagttcta    6540
gtgcagaaaa gtatgaggac acccttcact acatcggcga tcgtttccca gccggaagcc    6600
tcaccaatga tggcgtcgga atgccacttc ttcctcttag aaaacgtgat ccaattcaag    6660
gttcgaatta tggtttcgga acccttgact tctccgaata catcgtccgc aatccgaatc    6720
gcgttcttcc aaagtatatt gtcatgtata agtaattgat tccactacct cccccgtca    6780
tgactctctt ccacattaat cataaatctc atgttttgaa taatgtatca atagttattc    6840
cgcaaaatta ataagagattt gtacttaaaa aaaaaaaaa aaaaa                    6885
```

<210> SEQ ID NO 7
<211> LENGTH: 945
<212> TYPE: PRT
<213> ORGANISM: Artificial Sequence
<220> FEATURE:
<221> NAME/KEY: PEPTIDE
<222> LOCATION: (1)...(945)
<223> OTHER INFORMATION: PME-1

<400> SEQUENCE: 7

```
Met Ile His Ser Asn Glu Pro Leu Pro Tyr Ala Ile Glu Tyr Ala Lys
  1               5                  10                  15

Ser Gly Arg Ser Asn Cys Lys Thr Cys Lys Lys Asn Ile Ala Leu Asp
             20                  25                  30

Gln Leu Arg Met Ser Met Asn Arg Pro Ser Thr Phe Phe Asp Gly Asn
         35                  40                  45

Met Asp Ser Trp Phe His Tyr Asn Cys Phe Trp Ile Lys Met Ile Arg
 50                  55                  60

Gly Arg Asp Asp Ile Asn Ile Ser Ser Ile Arg Gly Val Asp Trp Leu
 65                  70                  75                  80

Arg Trp Glu Asp Gln Glu Lys Leu Arg Gln Glu Ile Gln His Phe Lys
                 85                  90                  95

Thr Ala Ser Pro Pro Thr Leu Thr Pro Leu Cys Ser Thr Thr Thr Val
            100                 105                 110

Ile Leu Ser Thr Ile Lys Thr Glu Lys Ser Leu Ser Asn Arg Gly Lys
        115                 120                 125

Cys Gly Lys Cys Gly Gln Asn Phe Glu Arg Gly Glu Ile Lys Ala His
130                 135                 140

Asn Lys Gly Lys Ala Asn His Leu Asn Cys Phe Leu Gln Glu Phe Asp
145                 150                 155                 160

Lys Ile Ser Gly Thr Val Glu Asp Ile Pro Gly Trp Ala Asp Tyr Glu
                165                 170                 175

Glu Asn Phe Lys Ile Lys Ala Val Gly Glu Tyr Val Glu Ala Leu Ala
            180                 185                 190

Ala Lys Arg Arg Ser Thr Glu Pro Ala Thr Pro Ala Ser Ala Ser Pro
        195                 200                 205

Thr Pro Pro Glu Ala Glu Thr Pro Val Leu Ser Ala Glu Gly Ser Pro
    210                 215                 220

Glu Ser Ser Asn Lys Arg Pro Ala Ser Ser Glu Ile Ile Glu Ile Asp
225                 230                 235                 240

Gly Glu Gly Asn Pro Asp Glu Asn Asp Phe Ala Lys Lys Arg Arg Met
                245                 250                 255

Lys Lys Glu Ala Arg Leu Met Glu Val Gln Lys Lys Arg Met Lys Lys
            260                 265                 270

Gln Ser Asp Leu Leu Trp Glu Tyr Arg Gln Ile Phe Glu Arg Met Pro
        275                 280                 285

Tyr Thr Asp Lys Ile Ser Ile Leu Arg Glu Asn Glu Gln Asp Ile Pro
    290                 295                 300

Glu Gly His Asp Pro Thr Ala Gln Val Ile Glu Arg Leu Val Asp Asn
305                 310                 315                 320

Ala Leu Phe Gly Cys Pro Ile Ile Cys Gln Thr Cys Ser Asn Gly Lys
                325                 330                 335

Ile Val Tyr Asn Ser Ser Cys Arg Thr Tyr Val Cys Thr Gly Tyr Ala
            340                 345                 350

Thr Glu Tyr Ser Lys Cys Thr Tyr Glu Ser Lys Asn Pro Ile Arg Thr
        355                 360                 365

Pro Phe Glu Val Ser His Arg Leu Thr Glu Lys His Lys Leu Gln Asp
    370                 375                 380

Ile Val Phe Asn Gln Met Ser Glu Arg Leu Tyr Ile Gly Glu Glu Asp
385                 390                 395                 400

Gly Glu Ser Val Val Lys Ile Asp Lys Arg Lys Ser Lys Gly Gly Thr
```

```
                    405                 410                 415
Arg Gly Glu Gln Phe Ile Tyr Ala Ala Glu Ala Phe Asp Ser Thr Asn
            420                 425                 430

Asn Val Pro Ile Lys Val Gly Asp Leu Thr Ser Thr Asn Thr His Ile
            435                 440                 445

Ile Lys Lys Gly Thr Val Val Asp Ala Lys Phe Ala Leu Ala Asp Arg
            450                 455                 460

Cys His Val Phe Lys Asn Glu Ile Asp Gly Ser Leu Tyr Gln Ala Thr
465                 470                 475                 480

Leu Ser Phe Thr Asp Leu Thr Gln Asn Lys Asn Ser Tyr Tyr Lys Ile
                485                 490                 495

Gln Leu Leu Lys Asp Asp Gln Arg Glu Asn Tyr Tyr Val Phe Arg Ser
            500                 505                 510

Trp Gly Arg Val Gly Thr Glu Val Gly Asn Lys His Glu Ser Tyr
            515                 520                 525

Ser Asn Ser Asn Glu Ala Ile Leu Lys Phe Gln Asp Val Phe His Glu
            530                 535                 540

Lys Thr Lys Asn Asp Trp Ile Tyr Arg Lys His Phe Arg Lys Met Pro
545                 550                 555                 560

Gly Met Phe Ser Tyr Val Glu Thr Asp Tyr Ser Glu Phe Ala Gln Ile
                565                 570                 575

Thr Asp Thr Glu Ile Thr Pro Gly Ser Lys Thr Leu Leu Pro Lys Ser
                580                 585                 590

Val Lys Glu Val Val Met Ser Ile Phe Asp Val Glu Asn Met Lys Ser
            595                 600                 605

Ala Leu Lys Ser Phe Glu Met Asp Val Asn Lys Met Pro Leu Gly Arg
            610                 615                 620

Leu Ser His Asn Gln Ile Asn Leu Ala Phe Glu Val Leu Asn Asp Ile
625                 630                 635                 640

Ser Asp Leu Leu Val Lys Leu Pro Ile Asp Ala Ser Arg Ile Leu Asp
                645                 650                 655

Phe Ser Asn Lys Phe Tyr Thr Ile Ile Pro His Asn Phe Gly Met Arg
                660                 665                 670

Val Pro Glu Pro Ile Asp Ser Phe His Lys Ile Lys Glu Lys Asn Asn
            675                 680                 685

Met Leu Asn Ala Leu Leu Asp Ile Lys Phe Ala Tyr Asp Gln Ile Ser
            690                 695                 700

Gly Gly Asp Val Pro Ala Ser Thr Ser Leu Gly Ile Asp Pro Val Asp
705                 710                 715                 720

Ile Asn Tyr Gln Lys Leu Lys Cys Ile Met Glu Pro Leu Gln Gln Gly
                725                 730                 735

Cys Asp Asp Trp Asn Met Ile His Gln Tyr Leu Lys Asn Thr His Gly
                740                 745                 750

Ala Thr His Asp Leu Lys Val Glu Leu Ile Asp Ile Leu Lys Leu Asn
            755                 760                 765

Arg Asp Asn Glu Ser Ser Lys Phe Lys Arg His Ile Gly Asn Arg Arg
            770                 775                 780

Leu Leu Trp His Gly Ser Gly Lys Met Asn Phe Ala Gly Ile Leu Gly
785                 790                 795                 800

Gln Gly Leu Arg Ile Ala Pro Pro Glu Ala Pro Val Ser Gly Tyr Met
                805                 810                 815

Phe Gly Lys Gly Val Tyr Phe Ala Asp Met Phe Ser Lys Ser Phe Phe
            820                 825                 830
```

-continued

Tyr Cys Arg Ala Asn Ala Lys Glu Glu Ala Tyr Leu Leu Leu Cys Asp
            835                 840                 845

Val Ala Leu Gly Asn Val Gln Gln Leu Met Ala Ser Lys Asn Val Ser
850                 855                 860

Arg Gln Thr Leu Pro Ala Gly Phe Gln Ser Val Gln Gly Leu Gly Arg
865                 870                 875                 880

Gln Cys Pro Arg Glu Ile Gly Ser Tyr Asn His Pro Asp Gly Tyr Thr
                885                 890                 895

Ile Pro Leu Gly Leu Thr Tyr Met Gln Leu Gln Gly Lys Gln Asp Val
                900                 905                 910

Asp Tyr His Leu Leu Tyr Asn Glu Phe Ile Val Tyr Asp Val Asp Gln
            915                 920                 925

Ile Gln Leu Lys Tyr Leu Val Arg Val Lys Met His His Ala Arg His
            930                 935                 940

Leu
945

<210> SEQ ID NO 8
<211> LENGTH: 538
<212> TYPE: PRT
<213> ORGANISM: Artificial Sequence
<220> FEATURE:
<221> NAME/KEY: PEPTIDE
<222> LOCATION: (1)...(538)
<223> OTHER INFORMATION: PME-2

<400> SEQUENCE: 8

Met Ser Ile Ile Asn Asp Glu Asn Gly Arg Gly Tyr Lys Val His Leu
 1               5                  10                  15

Cys Lys Thr Asn Ile Ala Gln Asn Asn Lys Phe Tyr Asp Met Glu
            20                  25                  30

Leu Leu Asp Glu Gly Gly Asp Phe Ile Val Lys Leu Ile Asn Gly Arg
            35                  40                  45

Ile Gly Tyr Arg Gly Val Thr Gln Leu Lys Asp Phe Asp Asp Leu Asp
 50                  55                  60

Arg Ala Lys Lys Phe Phe Glu Ser Lys Phe Tyr Glu Lys Thr His Leu
65                  70                  75                  80

His Trp Glu Glu Arg Asp Asp Glu Pro Val Pro Asn Lys Tyr Ala Val
                85                  90                  95

Val Glu Leu Ala Thr Asn Ala Arg Gln Thr Glu Lys Glu Val Lys Lys
            100                 105                 110

Glu Glu Pro Glu Pro Glu Pro Lys Val Asp Glu Lys Asn Thr Arg Gly
        115                 120                 125

Arg Lys Lys Arg Gly Ile Val Lys Glu Lys Lys Glu Ile Lys Lys Glu
    130                 135                 140

Glu Glu Pro Val Glu Glu Val Asn Glu Lys Leu Lys Glu Leu Met Lys
145                 150                 155                 160

Cys Ile Cys Asp Glu Asp Val His Leu Gly Leu Leu Lys Gln Leu Lys
                165                 170                 175

Phe Asn Glu Ala Phe Gly Arg Pro Ile Asp Cys Leu Ser Leu Ala Gln
            180                 185                 190

Leu Thr Thr Gly Tyr Glu Ile Leu Ser Lys Ile Glu Glu Ser Ile Gly
        195                 200                 205

Gly Lys Ser Ala Arg Arg Ser Thr Arg Gly Arg Pro Arg Val Ala Asp
    210                 215                 220

```
Arg Val Leu Ala Val Lys Ser Asp Gly Pro Ser Leu His Asp Ile Asn
225                 230                 235                 240

Lys Tyr Tyr Ser Leu Ile Pro His Ser Phe Gly Phe Cys Val Pro Pro
            245                 250                 255

Lys Ile Asp Ser His Ala Lys Ile Gln Ala Glu Arg Glu Leu Leu Asp
        260                 265                 270

Ala Leu Lys Gly Ser Ile Glu Ala Ser Leu Glu Leu Lys Asp Leu Lys
    275                 280                 285

Lys Thr Ala Ser Ser Lys Asp Ile Tyr Gln Arg Leu Tyr Glu Arg Leu
290                 295                 300

Pro Cys His Leu Glu Pro Val Ser Glu Glu Ile Ala Gly Lys Ile Gly
305                 310                 315                 320

Asp Cys Leu Ala Met Arg Gly Pro Thr His Cys Tyr Lys Leu Ser Leu
                325                 330                 335

Ile Asp Ala Phe Glu Leu Lys Asp Pro Asn Glu Ile Pro Thr Glu Ala
            340                 345                 350

Pro Val Glu Val Gln Glu Val Pro Lys Lys Arg Gly Arg Lys Ser Thr
        355                 360                 365

Lys Thr Ala Ala Pro Thr Val Pro Pro Thr Thr Lys Arg Leu Leu
370                 375                 380

Trp His Gly Thr Arg Val Thr Asn Val Phe Ser Ile Leu Met Asn Gly
385                 390                 395                 400

Leu Gln Phe Pro Val Gly Asp Arg Cys Gly Leu Met Phe Gly Asn Gly
                405                 410                 415

Val Tyr Phe Ala Asn Val Pro Thr Lys Ser Ala Asn Tyr Cys Cys Pro
            420                 425                 430

Glu Ala Ser Lys Arg Val Phe Met Leu Leu Cys Glu Val Glu Thr Ala
        435                 440                 445

Asn Pro Leu Val Leu Tyr Glu Ser Glu Ile Asp Ala Asp Glu Lys Met
450                 455                 460

Glu Lys Ala Lys Lys Thr Ser Val Tyr Ala Ala Gly Lys His Thr Pro
465                 470                 475                 480

Arg Asp Thr Val Glu Ile Asn Gly Ile Pro Ala Phe Lys Ser Asn Leu
                485                 490                 495

Glu Thr Ile Glu Glu Thr Arg Leu Leu Tyr Asp Glu Tyr Val Met
        500                 505                 510

Phe Asn Lys Glu His Phe Lys Ile Lys Tyr Val Val Glu Val Lys Val
    515                 520                 525

Asp Arg Leu Thr Ala Lys Glu Met Met Ala
530                 535
```

<210> SEQ ID NO 9
<211> LENGTH: 781
<212> TYPE: PRT
<213> ORGANISM: Artificial Sequence
<220> FEATURE:
<221> NAME/KEY: PEPTIDE
<222> LOCATION: (1)...(781)
<223> OTHER INFORMATION: PME-3L

<400> SEQUENCE: 9

```
Met Ser Lys Lys Phe Ile Glu Leu Gly Asp Pro Val Thr Gln Asp Glu
1               5                   10                  15

Lys Asp Tyr Glu Asp Tyr Val Gly Val Gly Phe Ala His Gln Val Pro
            20                  25                  30

Thr Met Lys Arg Arg Lys Leu Thr Glu His Gly Asn Thr Thr Glu Ser
```

-continued

```
               35                  40                  45
Lys Glu Asp Pro Glu Pro Lys Ser Arg Asp Val Phe Val Ser Ser
             50                  55                  60
Gln Ser Ser Asp Glu Ser Gln Glu Asp Ser Ala Glu Asn Pro Glu Ile
 65                  70                  75                  80
Ala Lys Glu Val Ser Glu Asn Cys Glu Asn Leu Thr Glu Thr Leu Lys
                 85                  90                  95
Ile Ser Asn Ile Glu Ser Leu Asp Asn Val Thr Glu Arg Ser Glu His
                100                 105                 110
Thr Leu Asp Asn His Lys Ser Thr Glu Pro Met Glu Glu Asp Val Asn
                115                 120                 125
Asn Lys Ser Asn Ile Asp Val Ala Ile Asn Ser Asp Glu Asp Asp Glu
130                 135                 140
Leu Val Leu Glu Glu Asn Asn Lys Glu Met Arg Asp Gly Glu Gln Val
145                 150                 155                 160
Gln Gln Asp Leu Phe Ala Asp Gln Glu Leu Ile Glu Tyr Pro Gly
                165                 170                 175
Ile Met Lys Asp Thr Thr Thr Gln Leu Asp Ile Thr Asp Ser Glu Val
                180                 185                 190
Glu Thr Ala Gln Lys Met Glu Met Ile Glu Glu Thr Glu Ala Asp Ser
                195                 200                 205
Thr Phe Val Gly Glu Asp Ser Lys Asn Gln Arg Gln Ser Gly Thr Thr
210                 215                 220
Ser Asp Glu Val Asp Ala Asp Ser Gln Ile Asn Leu Ala Thr Lys Thr
225                 230                 235                 240
Val Arg Thr Ser Ser Ser Ser Phe Leu Ser Thr Val Ser Thr Cys Glu
                245                 250                 255
Ala Pro Ala Lys Gly Arg Ala Arg Met Tyr Gln Lys Glu Leu Glu Lys
                260                 265                 270
His Val Ile Ala Phe Thr Glu Gly Asn Leu Thr Leu Gln Pro Asp Leu
                275                 280                 285
Asn Lys Val Asp Pro Asp Arg Asn Tyr Arg Tyr Cys Thr Ile Pro Asn
290                 295                 300
Phe Pro Ala Ser Gln Gly Lys Leu Arg Glu Asp Asn Arg Tyr Gly Pro
305                 310                 315                 320
Lys Ile Val Leu Pro Gln Arg Trp Arg Glu Phe Asp Ser Arg Gly Arg
                325                 330                 335
Arg Arg Asp Ser Tyr Phe Tyr Phe Lys Arg Lys Leu Asp Gly Tyr Leu
                340                 345                 350
Lys Cys Tyr Lys Thr Thr Gly Tyr Phe Met Phe Val Gly Leu Leu His
                355                 360                 365
Asn Met Trp Glu Phe Asp Pro Asp Ile Thr Tyr Lys Leu Pro Ala Leu
370                 375                 380
Glu Met Tyr Tyr Lys Glu Met Ser Glu Leu Val Gly Arg Glu Glu Val
385                 390                 395                 400
Leu Glu Lys Phe Ala Arg Val Ala Arg Ile Ala Lys Thr Ala Glu Asp
                405                 410                 415
Ile Leu Pro Glu Arg Ile Tyr Arg Leu Val Gly Asp Val Glu Ser Ala
                420                 425                 430
Thr Leu Ser His Lys Gln Cys Ala Ala Leu Val Ala Arg Met Phe Phe
                435                 440                 445
Ala Arg Pro Asp Ser Pro Phe Ser Phe Cys Arg Ile Leu Ser Ser Asp
450                 455                 460
```

Lys Ser Ile Cys Val Glu Lys Leu Lys Phe Leu Phe Thr Tyr Phe Asp
465                 470                 475                 480

Lys Met Ser Met Asp Pro Asp Gly Ala Val Ser Phe Arg Leu Thr
            485                 490                 495

Lys Met Asp Lys Asp Thr Phe Asn Glu Glu Trp Lys Asp Lys Lys Leu
            500                 505                 510

Arg Ser Leu Pro Glu Val Glu Phe Phe Asp Glu Met Leu Ile Glu Asp
            515                 520                 525

Thr Ala Leu Cys Thr Gln Val Asp Phe Ala Asn Glu His Leu Gly Gly
            530                 535                 540

Gly Val Leu Asn His Gly Ser Val Gln Glu Glu Ile Arg Phe Leu Met
545                 550                 555                 560

Cys Pro Glu Met Met Val Gly Met Leu Leu Cys Glu Lys Met Lys Gln
                565                 570                 575

Leu Glu Ala Ile Ser Ile Val Gly Ala Tyr Val Phe Ser Ser Tyr Thr
            580                 585                 590

Gly Tyr Gly His Thr Leu Lys Trp Ala Glu Leu Gln Pro Asn His Ser
            595                 600                 605

Arg Gln Asn Thr Asn Glu Phe Arg Asp Arg Phe Gly Arg Leu Arg Val
            610                 615                 620

Glu Thr Ile Ala Ile Asp Ala Ile Leu Phe Lys Gly Ser Lys Leu Asp
625                 630                 635                 640

Cys Gln Thr Glu Gln Leu Asn Lys Ala Asn Ile Ile Arg Glu Met Lys
            645                 650                 655

Lys Ala Ser Ile Gly Phe Met Ser Gln Gly Pro Lys Phe Thr Asn Ile
            660                 665                 670

Pro Ile Val Thr Gly Trp Trp Gly Cys Gly Ala Phe Asn Gly Asp Lys
            675                 680                 685

Pro Leu Lys Phe Ile Ile Gln Val Ile Ala Ala Gly Val Ala Asp Arg
690                 695                 700

Pro Leu His Phe Cys Ser Phe Gly Glu Pro Glu Leu Ala Ala Lys Cys
705                 710                 715                 720

Lys Lys Ile Ile Glu Arg Met Lys Gln Lys Asp Val Thr Leu Gly Met
            725                 730                 735

Leu Phe Ser Met Ile Asn Asn Thr Gly Leu Pro His Lys His Phe Glu
            740                 745                 750

Phe Tyr Val Phe Asp Arg Ile Ser Thr Tyr Leu Ser Ser Ser Glu Asp
            755                 760                 765

Val Glu Ser Ser Lys Ser Ser Pro Ser Val Ser Arg Ala
770                 775                 780

<210> SEQ ID NO 10
<211> LENGTH: 764
<212> TYPE: PRT
<213> ORGANISM: Artificial Sequence
<220> FEATURE:
<221> NAME/KEY: PEPTIDE
<222> LOCATION: (1)...(764)
<223> OTHER INFORMATION: PME-3S

<400> SEQUENCE: 10

Met Ser Lys Lys Phe Ile Glu Leu Gly Asp Pro Val Thr Gln Asp Glu
 1               5                  10                  15

Lys Asp Tyr Glu Asp Tyr Val Gly Val Gly Phe Ala His Gln Val Pro
            20                  25                  30

-continued

```
Thr Met Lys Arg Arg Lys Leu Thr Glu His Gly Asn Thr Thr Glu Ser
        35                  40                  45

Lys Glu Asp Pro Glu Pro Lys Ser Arg Asp Val Phe Val Ser Ser
 50                  55                  60

Gln Ser Ser Asp Glu Ser Gln Glu Asp Ser Ala Glu Asn Pro Glu Ile
 65                  70                  75                  80

Ala Lys Glu Val Ser Glu Asn Cys Glu Asn Leu Thr Glu Thr Leu Lys
                 85                  90                  95

Ile Ser Asn Ile Glu Ser Leu Asp Asn Val Thr Glu Arg Ser Glu His
            100                 105                 110

Thr Leu Asp Asn His Lys Ser Thr Glu Pro Met Glu Glu Asp Val Asn
            115                 120                 125

Asn Lys Ser Asn Ile Asp Val Ala Ile Asn Ser Asp Glu Asp Asp Glu
130                 135                 140

Leu Val Leu Glu Glu Asn Asn Lys Glu Met Arg Asp Gly Glu Gln Val
145                 150                 155                 160

Gln Gln Leu Ser Gln Asp Leu Phe Ala Asp Asp Gln Glu Leu Ile Glu
                165                 170                 175

Tyr Pro Gly Ile Met Lys Asp Thr Thr Thr Gln Leu Asp Ile Thr Asp
            180                 185                 190

Ser Glu Val Glu Thr Ala Gln Lys Met Glu Met Ile Glu Glu Thr Glu
            195                 200                 205

Ala Asp Ser Thr Phe Val Gly Glu Asp Ser Lys Ala Thr Lys Thr Val
        210                 215                 220

Arg Thr Ser Ser Ser Ser Phe Leu Ser Thr Val Ser Thr Cys Glu Ala
225                 230                 235                 240

Pro Ala Lys Gly Arg Ala Arg Met Tyr Gln Lys Glu Leu Glu Lys His
                245                 250                 255

Val Ile Ala Phe Thr Glu Gly Asn Leu Thr Leu Gln Pro Asp Leu Asn
            260                 265                 270

Lys Val Asp Pro Asp Arg Asn Tyr Arg Tyr Cys Thr Ile Pro Asn Phe
        275                 280                 285

Pro Ala Ser Gln Gly Lys Leu Arg Glu Asp Asn Arg Tyr Gly Pro Lys
290                 295                 300

Ile Val Leu Pro Gln Arg Trp Arg Glu Phe Asp Ser Arg Gly Arg Arg
305                 310                 315                 320

Arg Asp Ser Tyr Phe Tyr Phe Lys Arg Lys Leu Asp Gly Tyr Leu Lys
                325                 330                 335

Cys Tyr Lys Thr Thr Gly Tyr Phe Met Phe Val Gly Leu Leu His Asn
            340                 345                 350

Met Trp Glu Phe Asp Pro Asp Ile Thr Tyr Lys Leu Pro Ala Leu Glu
            355                 360                 365

Met Tyr Tyr Lys Glu Met Ser Glu Leu Val Gly Arg Glu Glu Val Leu
        370                 375                 380

Glu Lys Phe Ala Arg Val Ala Arg Ile Ala Lys Thr Ala Glu Asp Ile
385                 390                 395                 400

Leu Pro Glu Arg Ile Tyr Arg Leu Val Gly Asp Val Glu Ser Ala Thr
                405                 410                 415

Leu Ser His Lys Gln Cys Ala Ala Leu Val Ala Arg Met Phe Phe Ala
            420                 425                 430

Arg Pro Asp Ser Pro Phe Ser Phe Cys Arg Ile Leu Ser Ser Asp Lys
            435                 440                 445

Ser Ile Cys Val Glu Lys Leu Lys Phe Leu Phe Thr Tyr Phe Asp Lys
```

-continued

```
            450                 455                 460
Met Ser Met Asp Pro Pro Asp Gly Ala Val Ser Phe Arg Leu Thr Lys
465                 470                 475                 480

Met Asp Lys Asp Thr Phe Asn Glu Glu Trp Lys Asp Lys Lys Leu Arg
                485                 490                 495

Ser Leu Pro Glu Val Glu Phe Phe Asp Glu Met Leu Ile Glu Asp Thr
            500                 505                 510

Ala Leu Cys Thr Gln Val Asp Phe Ala Asn Glu His Leu Gly Gly Gly
        515                 520                 525

Val Leu Asn His Gly Ser Val Gln Glu Glu Ile Arg Phe Leu Met Cys
530                 535                 540

Pro Glu Met Met Val Gly Met Leu Leu Cys Glu Lys Met Lys Gln Leu
545                 550                 555                 560

Glu Ala Ile Ser Ile Val Gly Ala Tyr Val Phe Ser Ser Tyr Thr Gly
                565                 570                 575

Tyr Gly His Thr Leu Lys Trp Ala Glu Leu Gln Pro Asn His Ser Arg
            580                 585                 590

Gln Asn Thr Asn Glu Phe Arg Asp Arg Phe Gly Arg Leu Arg Val Glu
        595                 600                 605

Thr Ile Ala Ile Asp Ala Ile Leu Phe Lys Gly Ser Lys Leu Asp Cys
610                 615                 620

Gln Thr Glu Gln Leu Asn Lys Ala Asn Ile Ile Arg Glu Met Lys Lys
625                 630                 635                 640

Ala Ser Ile Gly Phe Met Ser Gln Gly Pro Lys Phe Thr Asn Ile Pro
                645                 650                 655

Ile Val Thr Gly Trp Trp Gly Cys Gly Ala Phe Asn Gly Asp Lys Pro
            660                 665                 670

Leu Lys Phe Ile Ile Gln Val Ile Ala Ala Gly Val Ala Asp Arg Pro
        675                 680                 685

Leu His Phe Cys Ser Phe Gly Glu Pro Glu Leu Ala Ala Lys Cys Lys
690                 695                 700

Lys Ile Ile Glu Arg Met Lys Gln Lys Asp Val Thr Leu Gly Met Leu
705                 710                 715                 720

Phe Ser Met Ile Asn Asn Thr Gly Leu Pro His Lys His Phe Glu Phe
                725                 730                 735

Tyr Val Phe Asp Arg Ile Ser Thr Tyr Leu Ser Ser Ser Glu Asp Val
            740                 745                 750

Glu Ser Ser Lys Ser Ser Pro Ser Val Ser Arg Ala
        755                 760

<210> SEQ ID NO 11
<211> LENGTH: 485
<212> TYPE: PRT
<213> ORGANISM: Artificial Sequence
<220> FEATURE:
<221> NAME/KEY: PEPTIDE
<222> LOCATION: (1)...(485)
<223> OTHER INFORMATION: PME-4

<400> SEQUENCE: 11

Met Asp His Glu Asn Leu Met Lys Tyr Leu Glu Glu Phe Arg Ser Ile
1               5                   10                  15

Arg Phe Gln Pro Asp Phe Gln Lys Val Asp Ala Glu Arg Asn Val Arg
            20                  25                  30

Tyr Cys Glu Ile Thr Asp Phe Pro Ile Ser Asn Ile Ser Phe Glu Leu
        35                  40                  45
```

-continued

```
Leu Glu Thr Gly Val Ser Gln Gln Trp Arg Asn Cys Asp Gln Asn Leu
        50                  55                  60

Phe Asn Glu Tyr Leu Lys Thr Tyr Lys Asn Gly Gly Tyr Ser Gln Phe
 65                  70                  75                  80

Glu Asp Leu Leu Phe Lys Ile Trp Gly Tyr Ser Glu Lys Glu Arg
                 85                  90                  95

Phe Asp Leu Pro Ala Leu Lys Ser Phe Tyr Arg Lys Met Ser Glu Ile
            100                 105                 110

Val Gly Glu Asp Glu Val Leu Glu Lys Leu Ala Arg Leu Val Arg Ile
            115                 120                 125

Thr Lys Ser Ala Cys Glu Val Leu Pro Glu Lys Ile Tyr Arg Leu Val
        130                 135                 140

Gly Asp Ile Glu Ser Ala Thr Phe Ser His Ile Gln Cys Ala Ser Leu
145                 150                 155                 160

Ile Ala Trp Met Phe Phe Ser Asp Thr Pro Arg Leu Ser Phe Ile Ile
                165                 170                 175

Ile Leu Gln Lys Thr Thr Cys Val Ala Val Glu Lys Leu Lys Phe Leu
            180                 185                 190

Phe Thr Tyr Phe Asp Lys Met Ser Ile Asp Pro Ile Gly Ala Val
            195                 200                 205

Ser Phe Arg Lys Met Arg Ile Thr His Lys Gln Tyr Leu Glu Asn Trp
210                 215                 220

Lys Leu Arg Glu Thr Asn Leu Leu Pro Asp Val Gln Val Phe Asp Lys
225                 230                 235                 240

Met Ser Ile Glu Glu Thr Ala Leu Cys Thr Gln Ile Asp Phe Ala Asn
                245                 250                 255

Lys Arg Leu Gly Gly Val Leu Lys Gly Gly Ala Val Gln Glu Glu
            260                 265                 270

Ile Arg Phe Met Met Cys Pro Glu Met Met Val Ala Ile Leu Leu Asn
        275                 280                 285

Asp Val Thr Gln Asp Leu Glu Ala Ile Ser Ile Val Gly Ala Tyr Val
290                 295                 300

Phe Ser Ser Tyr Thr Gly Tyr Ser Asn Thr Leu Lys Trp Ala Lys Ile
305                 310                 315                 320

Thr Pro Lys His Ser Ala Gln Asn Asn Asn Ser Phe Arg Asp Gln Phe
                325                 330                 335

Gly Arg Leu Gln Thr Glu Thr Val Ala Ile Asp Ala Val Arg Asn Ala
            340                 345                 350

Gly Thr Pro Leu Glu Cys Leu Leu Asn Gln Leu Thr Thr Glu Lys Leu
        355                 360                 365

Thr Arg Glu Val Arg Lys Ala Ala Ile Gly Phe Leu Ser Ala Gly Asp
        370                 375                 380

Gly Phe Ser Lys Ile Pro Val Val Ser Gly Trp Trp Gly Cys Gly Ala
385                 390                 395                 400

Phe Arg Gly Asn Lys Pro Leu Lys Phe Leu Ile Gln Val Ile Ala Cys
                405                 410                 415

Gly Ile Ser Asp Arg Pro Leu Gln Phe Cys Thr Phe Gly Asp Thr Glu
            420                 425                 430

Leu Ala Lys Lys Cys Glu Glu Met Met Thr Leu Phe Arg Asn Asn Asn
        435                 440                 445

Val Arg Thr Gly Gln Leu Phe Leu Ile Ile Asn Ser Ile Gly Pro Pro
450                 455                 460
```

-continued

```
Leu Asn Tyr Ser Glu Gln Tyr Val Phe Asp Ala Ile Arg Ala Lys Ile
465                 470                 475                 480

Asn Ser Thr Lys Ala
            485

<210> SEQ ID NO 12
<211> LENGTH: 2238
<212> TYPE: PRT
<213> ORGANISM: Artificial Sequence
<220> FEATURE:
<221> NAME/KEY: PEPTIDE
<222> LOCATION: (1)...(2338)
<223> OTHER INFORMATION: PME-5

<400> SEQUENCE: 12

Met Ala Arg Arg Val Asn Lys Lys Ser Pro Val Lys Ala Ala Arg
 1               5                  10                  15

Lys Ile Asp Gly Gln Ile Gly Arg Arg Val Asp Gly Val Arg Ala
                20                  25                  30

Lys Ser Ser Arg Gln Arg His Gln Ala Val Leu Tyr Gln Ala Pro Thr
                35                  40                  45

Pro Thr Val Ile Arg Arg Lys Thr Thr Lys Thr Ala Ile Val Lys Lys
 50                  55                  60

Thr Val Val Val Lys Lys Gly Gly Lys Val Lys Lys Ser Ser
 65                  70                  75                  80

Lys Thr Gly Gln Lys Val Lys Ala Val Lys Ala Pro Lys Val Lys Ala
                85                  90                  95

Pro Ser Lys Lys Gly Asn Asp Arg Leu Thr Pro Arg Val Ile Thr Glu
                100                 105                 110

Tyr Gln Glu Asn Pro Phe Phe Tyr Asp Pro Gln Val Pro Glu Tyr Ile
                115                 120                 125

Ser Ala Ser Val Tyr His Arg Trp Ile Thr Arg Ala Val Arg Asn Gly
130                 135                 140

Asn Met Lys Glu Ile Lys Asp Tyr Tyr Lys Ser Lys Lys Cys Gln Lys
145                 150                 155                 160

Ser Ala Ile Tyr Thr Ser Phe Ala Tyr Ser Phe Asp Thr Ser Ala Cys
                165                 170                 175

Asp Glu Ala Leu Arg Gln Asp Ile Lys Phe Ala Thr Glu Phe Phe Lys
                180                 185                 190

Met Asn Asn Lys Met Glu Val Asp Asn Ser Tyr His Pro Gly Lys Glu
                195                 200                 205

Pro Asn Leu Leu Gln Lys Lys Thr Thr Gly Arg Lys Asn Tyr Tyr Met
                210                 215                 220

Leu Gly Arg His Thr Arg Gln Ile Glu Met Gly Arg Gly Gly Lys Glu
225                 230                 235                 240

Gly Asn Asn Ala Leu Leu Asn Tyr Asp Thr Arg Thr Asp Glu Pro Asn
                245                 250                 255

Pro Leu Thr Lys Leu Ile Glu Asp Asn Val Thr Tyr Thr Lys Leu Tyr
                260                 265                 270

Gln Leu Cys Lys Ile Pro Asp Gly Pro Ile Val Glu His His Ile Glu
                275                 280                 285

Met His Phe Val Thr Ala Val Arg Met Gly His Arg Asp Leu Ala Ser
                290                 295                 300

Ala Leu Ala Gln Gly Pro Val Lys Met His Cys Asn Asp Leu His Arg
305                 310                 315                 320

Ala Thr Leu Lys Asp Gln Lys Leu Pro Ala Lys Ile Leu Pro Val Ser
```

-continued

```
                325                 330                 335
Val Ala Lys Lys Ala Tyr Met Asn Lys Asn Ile Thr Pro Leu His Thr
            340                 345                 350
Ala Ala Ile Ser Asn Ser Thr His Met Leu Glu Ala Met Arg Ala Val
            355                 360             365
Tyr Pro Thr Ile Asn Ile Pro Asp Gln Asp Asn Trp Tyr Thr Met His
        370                 375                 380
Tyr Ala Ala Cys Ala Pro Gly Thr Ala Pro Met Glu Phe Leu Leu Lys
385                 390                 395                 400
Asn Gly Gly Ser Val Thr Met Leu Thr Lys Gln Thr Glu Thr Pro Leu
                405                 410                 415
His Val Ala Ala Arg Ala Gly Arg Ala Val Asn Cys Thr Phe Leu Met
            420                 425                 430
Lys Glu Met Leu Asp Leu Glu Lys Gly Asp Asp Gly Glu Ser Thr Ile
            435                 440                 445
Arg Ala Asp Arg Ser Ile Ile Asn Ala Arg Thr Arg Ser Gly Asn Ser
        450                 455                 460
Ala Leu His Leu Ala Val Leu Arg Asn Asn Leu Asp Val Val Asp Ala
465                 470                 475                 480
Leu Leu Ala Glu Pro Thr Ile Val Val Asp Asn Pro Thr Ser Thr Gly
                485                 490                 495
Gln Asn Arg Leu Thr Pro Leu Met Met Ala Cys Gly Lys Gly Tyr Leu
            500                 505                 510
Glu Met Ala Lys Lys Leu Val Glu Lys Gly Ala Leu Val Glu Gly Lys
            515                 520                 525
Asp Lys Lys Lys Arg Thr Pro Leu Ile His Ala Met Leu Asn Gly Gln
        530                 535                 540
Ile His Thr Ala Ala Phe Leu Leu Ala Lys Gly Ala Ser Leu Thr Leu
545                 550                 555                 560
Ala Asp Ser Ser Gly Asn Thr Ala Ala His Tyr Ala Ala Ala Tyr Gly
                565                 570                 575
Phe Leu Asp Cys Leu Lys Leu Leu Ala Ser Ile Asp Asp Asn Ile Leu
            580                 585                 590
Ser Glu Pro Asn Asp Trp Gln Leu Tyr Pro Leu Ser Val Ala Tyr Leu
            595                 600                 605
Lys Gly His Tyr Gly Ile Val Thr Trp Leu Leu Glu Gly Pro His Lys
        610                 615                 620
Asp Lys Ala Asn Ile Asn Ala Lys Asp Asn Asn Gly Ala Thr Leu Leu
625                 630                 635                 640
Ser Asn Leu Leu Ser Tyr Ala Asp Glu Thr Met His Lys Glu Leu Leu
                645                 650                 655
Ser Gln Ile Glu Tyr Leu Val Ala Arg Lys Ala Asp Ala Ser Leu Ala
            660                 665                 670
Asp Ser Ser Gly Gln Thr Pro Leu His Leu Phe Ser Met Gln Arg Ile
        675                 680                 685
Ile Leu Lys Gly Ser Gly Glu Ala Ala Glu Asn Asp Ala Met Arg Met
        690                 695                 700
Thr Leu Asp Asn Tyr Lys Lys Cys Phe Asn Thr Leu Ile Lys Ala Gly
705                 710                 715                 720
Ala Lys Val Asp Val Tyr Asp His Glu Asp Asn Thr Pro Leu His Tyr
                725                 730                 735
Ala Leu Thr Asn Gly Asn Leu Met Leu Phe Asn Leu Met Leu Asp Lys
            740                 745                 750
```

-continued

```
Val Ala Asn Lys Arg Asn Leu Phe Glu Lys Trp Ala Asn His Gln Asn
            755                 760                 765
Phe Leu His Glu Ile Leu Ala Leu Pro Met Lys Val Tyr Gly Asp Gln
    770                 775                 780
Val Leu Trp Lys Gly Glu Thr Leu Thr Lys Pro Ala Tyr Asp Val Leu
785                 790                 795                 800
Pro Ile Leu Lys Glu Leu His Glu Asn Leu Pro Asp Leu Phe Glu Lys
                805                 810                 815
Trp Ile Ser Glu Val Asn Lys Ala Gly Tyr Ser Pro Ile Val Glu Ala
            820                 825                 830
Ile Lys Gln Tyr Gln Ala Leu Ala Ala Asn Lys Lys Leu Arg Gly Glu
        835                 840                 845
Ala Asp Gln Thr Phe Ile Ser Thr Val Asn Glu Leu Phe Glu Trp Val
    850                 855                 860
Ile Arg Leu Gly Pro Phe Gln Leu Thr Gln Lys Tyr Ile Asn Ser Glu
865                 870                 875                 880
Asn Ser Ala Ala Val Thr Leu Ala Asn Leu Ala Met Ser Ile Pro Ile
                885                 890                 895
Glu Cys Gly Arg His Gln Gln Asn Gln Leu Ala Leu Phe Lys Ile Leu
            900                 905                 910
Ile Lys Leu Ser Lys Glu Phe Asn Lys Val Asp Glu Phe Leu Thr Gln
        915                 920                 925
Lys Asn Glu Lys Asp Asp Val Leu Ile Val Gln Ala Ile Met Phe Asp
    930                 935                 940
Lys Pro Asn Val Val Glu Leu Ile Leu Asp Thr Ala Ser Glu Met His
945                 950                 955                 960
Leu Ile His Gly Thr His Asn Ala Ile Lys Glu Asn Glu Leu Glu Val
                965                 970                 975
Val Val His Lys Thr Ile Ile Met Tyr Met Ile Glu Met Arg Met Trp
            980                 985                 990
Glu Leu Ile Pro Lys Val Asn Ala Ser Ser Glu Phe Trp Lys Ser Lys
        995                 1000                1005
Asp Ala Lys Gly Asn Ser Val Trp His Tyr Ala Ala Arg Val Asn Ser
    1010                1015                1020
His Lys Thr Val Gly Leu Phe Lys Met Ile Glu Ser Lys Gly Val Arg
1025                1030                1035                1040
Arg Glu Thr Asn Asp Asp Gly Arg Ser Val Leu His Val Ala Thr Leu
                1045                1050                1055
Ala Cys Asp Gly Ser Ala Asp Ser Val Leu Glu Pro Ile Ala Trp Leu
            1060                1065                1070
Ser Thr Arg Cys Pro Ile Asp Ala Val Asp Lys Phe Asn Arg Thr Ala
        1075                1080                1085
Leu His Tyr Ala Phe Gly Asn Gly Asn Asp Phe Lys Glu Gly Asn Val
    1090                1095                1100
Pro Phe Gly Glu Ser Asp Pro Ile Ala Val Val Ser Leu Leu Ser Ser
1105                1110                1115                1120
Leu Ile Arg Pro Glu Gln Ile Glu Ile Ala Asp Val Asn Gly Asn Thr
                1125                1130                1135
Ile Leu His Leu Ala Ala Ile Lys Asn Ser Thr Ile Cys Leu Met Thr
            1140                1145                1150
Leu Ile Arg Lys Lys Cys His Val Asp Leu Lys Asn Lys Asp Gly Asn
        1155                1160                1165
```

-continued

```
Thr Pro Leu Ala Leu Ala Val His His Gly Arg Gln Ser Ser Ala Leu
    1170            1175                1180
Thr Leu Ile Gln Ala Asn Ala Asp Val Thr Glu Lys Ile Phe Val Pro
1185                1190                1195                1200
Ala Leu Lys Pro Thr Ser Asp Phe Asp Gln Asn Ser Ser Gly Thr Glu
                1205                1210                1215
Ala Glu Lys Phe Trp Lys Trp His Gly Lys Glu Lys Lys Val Leu Glu
            1220                1225                1230
Asp Leu His Thr Thr Ile Pro Ala Ser Val Val Ser Lys Gly Gly Ser
        1235                1240                1245
Trp Glu Ala Met Val Tyr Val Leu Leu Asp Val Leu Gly Gln Asn Thr
    1250                1255                1260
Gly Ser Met Ala Gln Leu Thr Asp Ala Ala Leu Arg Arg Gly Gln Leu
1265                1270                1275                1280
Asn Leu Ala Asn Gln Leu Leu Lys Ser Ile Glu Ala Leu Ile Asp Gly
                1285                1290                1295
Ala Val Leu Asn Ser Ser Tyr Asp Leu Leu Asp Thr Phe Ala Glu Lys
            1300                1305                1310
Cys Phe Gly Ala Leu Thr Ser Glu Glu Thr Ile Glu Lys Thr Val Leu
        1315                1320                1325
Asn Arg Ile Ile Leu Thr Arg Gly Leu Gly Leu Lys Gln Pro Glu Thr
    1330                1335                1340
Met Lys Ile Ile Arg Thr Ala Leu Gln Asn Gly Asn Trp Asn Leu Leu
1345                1350                1355                1360
Asn Phe Leu Lys Ser Glu Met Gly Thr Ala Trp Lys Asn Gln Lys Ile
                1365                1370                1375
Glu Thr Pro Thr Glu Asn Pro Ile Arg Ser Leu Leu Ile Tyr Met Asn
            1380                1385                1390
Glu Lys Ser Val Ser Ser Glu Ala Ile Gly Phe Leu Glu Glu Leu Arg
        1395                1400                1405
Gln Met Arg Gly Val Asn Ile Asp Ala Leu Cys Gln Leu Glu Ile Pro
    1410                1415                1420
Gly Lys Phe Lys Lys Ile Leu Asp Tyr Gly Leu Ile Pro Pro Ile Ser
1425                1430                1435                1440
Phe Ala Val Leu Gln Glu Asn Pro Asn Met Ile Arg Ala Leu Arg Asn
                1445                1450                1455
Ala Gly Ala Ser Leu Lys Thr Gln Asp Asp Tyr Gly Arg Thr Pro Leu
            1460                1465                1470
Met Tyr Ala Ile Met Thr Asn Asn Arg Ser Val Val Asp Ala Ile Val
        1475                1480                1485
Gly Asp Gly Lys Leu Ala Val Val Leu His Lys Gln Lys Ala Val Ala
    1490                1495                1500
Thr Gly Pro Arg Cys Val Ala Val Pro Met Arg Phe Gly Ala Thr Ser
1505                1510                1515                1520
Arg Ala Phe Ile Pro Ala Ala Ala Phe Ala Ser Val Pro Ala Arg Val
                1525                1530                1535
Glu Ser Asp Glu Glu Glu Asp Asn Ser Gly Ser Glu Ser Gly Glu
            1540                1545                1550
Asp Gly Ala Ala Ser Glu Asn Lys Ser Glu His Gly Ser Glu Asn Gly
        1555                1560                1565
Glu Ser Gly Asn Gly Ser Asp Asp Glu Asp Asp Asp Asp Asp Asp Ser
    1570                1575                1580
Ser Pro Pro Pro Ala Lys Lys Ser Arg Ile Ala Lys Glu Ala Ala Gly
```

-continued

```
            1585                1590                1595                1600

Pro Ser Thr Gly Pro Lys Arg Lys Leu Val Ile Thr Asp Pro Ser
                1605                1610                1615

Leu Phe Ser Ala Arg Asp His Lys Glu Asn Asn Pro Leu His Tyr Phe
            1620                1625                1630

Ile Glu Pro Leu Ala Trp Glu Asn Val Glu Leu Leu Gly Asp Leu Ala
            1635                1640                1645

Ala Ala Asn Lys Thr Ala Ile Val Gln Cys Leu Ile Asp Lys Arg Ser
        1650                1655                1660

Pro Asn Pro Ile Glu Leu Ala Ala Met Lys Met Asn Arg Arg Met Lys
1665                1670                1675                1680

Ser Glu Met Leu Lys Ile Val Lys Asn Ala Ala Phe Pro Arg Pro Ile
                1685                1690                1695

Lys Glu Thr Lys Leu Thr Leu Gln Gln Val His Ile Glu Pro Leu Ser
                1700                1705                1710

Asp Val Asp Glu Asp Ala Ala Lys Phe Leu Ala Lys Trp Val Glu Glu
            1715                1720                1725

Lys Asp Lys Lys Lys Thr Ser Glu Ala Pro Lys Pro His Lys Ser Ser
        1730                1735                1740

Thr Tyr Ser Thr Asn Gly Leu Val Ser Phe Cys Asp Glu Thr Gln Gln
1745                1750                1755                1760

Tyr Phe Asp Val Leu Met Asn Lys Thr Asp Leu Met Tyr Gly Arg Cys
                1765                1770                1775

Gly Phe His Asn Phe Tyr Arg Met Gln Ile Ile Lys Arg Arg Asp Ala
            1780                1785                1790

Glu Leu Phe Ile Leu Phe Thr Asn Trp Gly Arg Ile Gly Ser Gly Met
        1795                1800                1805

Gly Glu Phe Gln Thr Thr Pro Phe Asn Ser Leu Glu Leu Ala Ala Lys
    1810                1815                1820

Glu Phe Lys Ser Ile Phe Lys Ser Lys Ser Gly Asn Glu Trp Ala Pro
1825                1830                1835                1840

Leu Ala Asn Phe Arg Asp Met Pro Lys Lys Tyr Arg Leu Val Glu Thr
                1845                1850                1855

Asp Ser Thr Pro Thr Ser Leu Ala Glu Ile Glu Leu Thr Trp Lys Lys
                1860                1865                1870

Asn Thr Glu Lys Asp Pro Ile Arg Arg Met Ile Ala Asp Ile Ser Asp
            1875                1880                1885

Ala Lys Thr Leu Lys Thr Tyr Ala Ser Gln Val Gln Met Tyr Gly Gly
        1890                1895                1900

Ser Ser Gln Pro Phe Gly Arg Phe Thr Lys Glu Asn Ile Glu Lys Ala
1905                1910                1915                1920

Lys Leu Val Leu Asp Lys Leu Glu Lys Asn Ala Asn Arg Ile Lys Gln
                1925                1930                1935

Met Val Glu Ala Gln Thr Gly Val Val Glu Ser Asn Leu Leu Asp Ala
            1940                1945                1950

Tyr Ile Thr Thr Ser Glu Leu Ser Gly Asp Tyr Tyr Ser Leu Ile Pro
        1955                1960                1965

Ser Gly Glu Tyr Glu Phe Ser Asn Leu Thr Arg Leu Asp Asn Val Glu
    1970                1975                1980

Glu Ile Ala Arg His Arg Ala Arg Leu Asn Arg Cys Gln Glu Ile Glu
1985                1990                1995                2000

Thr Ala Thr Arg Leu Leu Cys Ala Ala Glu Phe Arg Gln Asp Leu Asp
                2005                2010                2015
```

-continued

```
Arg Val Asp Tyr Ile Arg Ser Ala Ile Gln Cys Glu Tyr Arg Leu Glu
            2020                2025                2030

Thr Pro Asp Ser Asp Ile Ser Gln Arg Leu Leu Gln Trp Ile His Asn
        2035                2040                2045

Ser Gly Gly Lys Gln Ala Lys Val Lys Met Ile Leu Glu Ile Ser Pro
        2050                2055            2060

Met Leu Ser Thr Glu Lys Phe Glu Pro Phe Val Asn Asp Asp Asn Gln
2065                2070                2075                2080

Lys Phe Leu Trp His Gly Thr Lys Ala Thr Asn Leu Met Ser Ile Leu
                2085                2090                2095

Lys Asn Gly Phe Leu Ile Asp Pro Pro Ser Ala Cys Lys Asn Gly Asn
            2100                2105                2110

Leu Phe Gly Ser Gly Ile Tyr Leu Ala Asp Ser Phe Glu Lys Ser Thr
            2115                2120            2125

His Tyr Cys Gln Pro Ser Ala Gly Gly Ile Asn Tyr Met Leu Val Cys
        2130                2135            2140

Gln Thr Ala Leu Gly Lys Val Arg Thr Leu Asp Thr Ile Pro Tyr His
2145                2150                2155            2160

Tyr Met Asn Gln Ser Ser Ser Ala Glu Lys Tyr Glu Asp Thr Leu
                2165                2170                2175

His Tyr Ile Gly Asp Arg Phe Pro Ala Gly Ser Leu Thr Asn Asp Gly
            2180                2185                2190

Val Gly Met Pro Leu Pro Leu Arg Lys Arg Asp Pro Ile Gln Gly
                2195                2200            2205

Ser Asn Tyr Gly Phe Gly Thr Leu Asp Phe Ser Glu Tyr Ile Val Arg
        2210                2215                2220

Asn Pro Asn Arg Val Leu Pro Lys Tyr Ile Val Met Tyr Lys
2225                2230                2235

<210> SEQ ID NO 13
<211> LENGTH: 34
<212> TYPE: DNA
<213> ORGANISM: Artificial Sequence
<220> FEATURE:
<221> NAME/KEY: primer_bind
<222> LOCATION: (1)...(34)
<223> OTHER INFORMATION: pme-4 forward primer

<400> SEQUENCE: 13
tatggatcca tggatcatga aaacttaatg aagt                              34

<210> SEQ ID NO 14
<211> LENGTH: 20
<212> TYPE: DNA
<213> ORGANISM: Artificial Sequence
<220> FEATURE:
<221> NAME/KEY: primer_bind
<222> LOCATION: (1)...(20)
<223> OTHER INFORMATION: pme-4 reverse primer

<400> SEQUENCE: 14
gttgagacac ccctgtttcc                                              20

<210> SEQ ID NO 15
<211> LENGTH: 21
<212> TYPE: DNA
<213> ORGANISM: Artificial Sequence
<220> FEATURE:
<221> NAME/KEY: primer_bind
<222> LOCATION: (1)...(21)
```

<223> OTHER INFORMATION: SL1 oligo-primer

<400> SEQUENCE: 15
gtttaattac ccaagtttga g                                        21

<210> SEQ ID NO 16
<211> LENGTH: 22
<212> TYPE: DNA
<213> ORGANISM: Artificial Sequence
<220> FEATURE:
<221> NAME/KEY: primer_bind
<222> LOCATION: (1)...(22)
<223> OTHER INFORMATION: SL2 oligo primer

<400> SEQUENCE: 16
ggttttaacc cagttactca ag                                       22

<210> SEQ ID NO 17
<211> LENGTH: 31
<212> TYPE: DNA
<213> ORGANISM: Artificial Sequence
<220> FEATURE:
<221> NAME/KEY: primer_bind
<222> LOCATION: (1)...(31)
<223> OTHER INFORMATION: cDNA library forward primer

<400> SEQUENCE: 17
tgtggatcca tgagcaagaa gtttatcgaa c                             31

<210> SEQ ID NO 18
<211> LENGTH: 26
<212> TYPE: DNA
<213> ORGANISM: Artificial Sequence
<220> FEATURE:
<221> NAME/KEY: primer_bind
<222> LOCATION: (1)...(26)
<223> OTHER INFORMATION: cDNA library reverse primer

<400> SEQUENCE: 18
gactgcgagg agacaaatac gtcacg                                   26

<210> SEQ ID NO 19
<211> LENGTH: 20
<212> TYPE: DNA
<213> ORGANISM: Artificial Sequence
<220> FEATURE:
<221> NAME/KEY: primer_bind
<222> LOCATION: (1)...(20)
<223> OTHER INFORMATION: pme-3 forward oligo-primer

<400> SEQUENCE: 19
agacactaca actcaactgg                                          20

<210> SEQ ID NO 20
<211> LENGTH: 20
<212> TYPE: DNA
<213> ORGANISM: Artificial Sequence
<220> FEATURE:
<221> NAME/KEY: primer_bind
<222> LOCATION: (1)...(20)
<223> OTHER INFORMATION: pme-3 reverse oligo-primer

<400> SEQUENCE: 20
tgacaggaaa cttgaactgg                                          20

<210> SEQ ID NO 21
<211> LENGTH: 37

```
<212> TYPE: DNA
<213> ORGANISM: Artificial Sequence
<220> FEATURE:
<221> NAME/KEY: primer_bind
<222> LOCATION: (1)...(37)
<223> OTHER INFORMATION: pme-3 cDNA library forward oligo-primer

<400> SEQUENCE: 21
ttgtccatgg gtaccatgag caagaagttt atcgaac                              37

<210> SEQ ID NO 22
<211> LENGTH: 20
<212> TYPE: DNA
<213> ORGANISM: Artificial Sequence
<220> FEATURE:
<221> NAME/KEY: primer_bind
<222> LOCATION: (1)...(20)
<223> OTHER INFORMATION: pme-3 cDNA library reverse oligo-primer

<400> SEQUENCE: 22
ttgaagttct gcccatttta                                                 20

<210> SEQ ID NO 23
<211> LENGTH: 34
<212> TYPE: DNA
<213> ORGANISM: Artificial Sequence
<220> FEATURE:
<221> NAME/KEY: primer_bind
<222> LOCATION: (1)...(34)
<223> OTHER INFORMATION: pme-4 cDNA library forward oligo-primer

<400> SEQUENCE: 23
tatggatcca tggatcatga aaacttaatg aagt                                 34

<210> SEQ ID NO 24
<211> LENGTH: 26
<212> TYPE: DNA
<213> ORGANISM: Artificial Sequence
<220> FEATURE:
<221> NAME/KEY: primer_bind
<222> LOCATION: (1)...(26)
<223> OTHER INFORMATION: pme-4 cDNA library reverse oligo-primer

<400> SEQUENCE: 24
tgtaagcttt gctttggtgg aattga                                          26

<210> SEQ ID NO 25
<211> LENGTH: 20
<212> TYPE: DNA
<213> ORGANISM: Artificial Sequence
<220> FEATURE:
<221> NAME/KEY: primer_bind
<222> LOCATION: (1)...(20)
<223> OTHER INFORMATION: gk120 mutation forward primer

<400> SEQUENCE: 25
attttgacaa ggcgagagga                                                 20

<210> SEQ ID NO 26
<211> LENGTH: 20
<212> TYPE: DNA
<213> ORGANISM: Artificial Sequence
<220> FEATURE:
<221> NAME/KEY: primer_bind
<222> LOCATION: (1)...(20)
<223> OTHER INFORMATION: gk120-2 forward primer

<400> SEQUENCE: 26
```

```
caggccattt tttgagccgt                                                   20
```

<210> SEQ ID NO 27
<211> LENGTH: 20
<212> TYPE: DNA
<213> ORGANISM: Artificial Sequence
<220> FEATURE:
<221> NAME/KEY: primer_bind
<222> LOCATION: (1)...(20)
<223> OTHER INFORMATION: gk120 reverse primer

<400> SEQUENCE: 27

```
tctgggtcaa attcccacat                                                   20
```

<210> SEQ ID NO 28
<211> LENGTH: 22
<212> TYPE: DNA
<213> ORGANISM: Artificial Sequence
<220> FEATURE:
<221> NAME/KEY: primer_bind
<222> LOCATION: (1)...(22)
<223> OTHER INFORMATION: pme-31 forward primer

<400> SEQUENCE: 28

```
ggtttaatta cccaagtttg ag                                                22
```

<210> SEQ ID NO 29
<211> LENGTH: 46
<212> TYPE: DNA
<213> ORGANISM: Artificial Sequence
<220> FEATURE:
<221> NAME/KEY: primer_bind
<222> LOCATION: (1)...(46)
<223> OTHER INFORMATION: pme-31 reverse primer

<400> SEQUENCE: 29

```
gcagaaatag actttcacaa aacacatcga cacatcgaca cttcga                      46
```

METHOD OF LETHALLY SENSITIZING HUMAN AND ANIMAL CELLS

This application claims priority on U.S. application Ser. No. 60/468,261 filed May 7, 2003, the entire content of which is hereby incorporated by reference.

BACKGROUND OF THE INVENTION a) Field of the Invention

The present invention relates to the field of sensitizing human and animal target cells to external dead inducer. The invention particularly relates to method and a composition for inhibiting or neutralizing DNA sequences and corresponding polypeptides thereof, therefore causing sensitization of cells to subsequent treatment by external killing elements, such as chemical entities or radiations.

b) Description of the Prior Art

Post-translational modifications regulate key functions performed by specialized proteins. Poly(ADP-ribosyl)ation, an emerging post-translational modification, is thought to regulate many nuclear functions, including DNA repair, replication and transcription, chromatin structure and apoptosis. Poly(ADP-ribosyl)ation resembles phosphorylation in that: 1) functional groups are added to certain amino acids residues of their target proteins, and 2) both involved two groups of enzymes working in tandem. Poly(ADP-ribosyl)ation metabolism is made possible by the concerted action of poly(ADP-ribose) polymerases (PARPs) and poly(ADP-ribose) glycohydrolase (PARG).

Different members of the PARP family have been described in the art, such as canonical PARP-1, PARP-2, PARP-3, VPARP, tankyrase-1 and -2, and TiPARP. The PARPs enzymes catalyze the transfer, polymerization and branching of ADP-ribose moiety from $NAD^+$ into poly (ADP-ribose) polymers. The substrate $NAD^+$ is used, in this case, as a building block rather than as an electron transporter. Polymers of broad length ranging from 2 to hundreds of units of ADP-ribose are covalently attached to glutamate residues of many proteins such as histones, PARPs themselves and topoisomerases. PARP-1 and PARP-2, both nuclear enzymes, have their enzymatic activities dramatically stimulated by DNA strand breaks. Although PARP-1 has been shown to be involved in base excision DNA-repair, it has been demonstrated that PARP-1 may not be essential for single-strand breaks repair but might well be involved in the expression of essentials DNA-repair factors. The function(s) of tankyrases is (are) still debated and may either be involved in telomeres metabolism or vesicular transport or both. The roles and function of others PARP members are still under investigation.

Catabolism of poly(ADP-ribose) is conveyed mainly by PARG and, to a lesser extent, by the enzyme ADP-ribosyl protein lyase. The latter catalyzes the removal of the most proximal ADP-ribose residue on the modified protein and seem to be the rate-limiting step of poly(ADP-ribose) degradation. PARG activity was first observed in calf thymus extracts, as suggested by the cleavage of the ribose-ribose bond of pADPr. PARG as known in the art also hydrolyzes the branch points of pADPr. Nonetheless, PARG is specific to pADPr as it cannot hydrolyze the ribose-ribose bond of Ado(P)-Rib(P) or Ado(P)-Rib(P)-Rib(P). The half-life of pADPr is less than one minute in cells treated with alkylating agents such as MNNG. The polymer is thus quickly processed by PARG through endo- and exoglycosidic modes of action. The recent cloning of PARG in human, bovine, mouse, and rat provided the first evidence that the PARG enzyme was synthesized as a single polypeptide. Immunolocalization of PARG enzyme shows it to be at a perinuclear location in the cytoplasm away from the main cellular site of poly(ADP-ribosyl)ation, the nucleus, where PARP-1 and PARP-2 reside. This suggests that catabolism of poly(ADP-ribose) may involve components of the nuclear import/export system.

Little is known on the physiological role of PARG. Studies with the PARG inhibitors gallotanin and nobotanin B showed a protective effect on oxidative and excitotoxic neuronal death. This suggests that PARG is an activator of cell death in certain cell type. A mutation called tej, localized in the *Arabidopsis thaliana* PARG gene, was shown to interfere with the circadian cycle. This study showed for the first time a relationship between poly(ADP-ribosyl)ation and pace regulation of circadian oscillator.

PARP inhibitors have been reported to be effective in radiosensitizing hypoxic tumor cells and also effective in preventing tumor cells from recovering from potentially lethal damage of DNA after radiation therapy, presumably by their ability to prevent DNA repair.

U.S. Pat. No. 5,032,617, U.S. Pat. No. 5,041,653 and U.S. Pat. No. 5,215,738 disclose compositions and methods for radiosensitizing hypotoxic tumor cells by using benzamide derivatives and nicotinamide compounds. Nevertheless, data are given only on survival rate of tumor cells having been prior sensitized and irradiated in vivo. It is not possible to know whether the survival of animals treated for killing tumor cells was higher than animals not having been treated.

U.S. patent application Ser. No. 200030078212 discloses a pharmaceutical composition containing PARP inhibitors and their uses, resulting in the prevention of a disease resulting from cell damage or death.

According to the state of the art described above, there are still needs to be provide new methods and compositions allowing the targeted killing of cells in an animal or a human.

SUMMARY OF THE INVENTION

One aim of the present invention is to provide an isolated DNA sequence having the sequence selected from the group consisting of SEQ ID NO:1, SEQ ID NO:2, SEQ ID NO:3, SEQ ID NO:4, SEQ ID NO:5, and SEQ ID NO:6, or a fragment thereof. The isolated encoding DNA sequences can be selected for a polypeptide having the amino acid sequence selected from the group consisting of SEQ ID NO:7, SEQ ID NO:8, SEQ ID NO:9, SEQ ID NO:10, SEQ ID NO:11, and SEQ ID NO:12, or a fragment thereof.

Another aim of the present invention is to provide a method for killing human or animal cells comprising the steps of:

a) submitting human or animal cells to an inhibitor of activity or expression in said cells, of a polypeptide having the amino acid sequence as depicted in SEQ ID NO:7, SEQ ID NO:8, SEQ ID NO:9, SEQ ID NO:10, SEQ ID NO:11, and SEQ ID NO:12, or a fragment thereof for causing sensitization of said cells;

b) treating cells sensitized in step a) with a dose of a chemical entity or irradiation effective to kill said cells.

For the purpose of the present invention the following terms are defined below.

The term "RNAi" is intended to mean RNA interference. It is generally admitted that this is a type of post-transcriptional gene silencing (PTGS) induced directly into living cells by double-stranded RNA. The general cellular transcription process is unaffected, but the gene expression is lost because mRNA molecules become unstable and degraded prior to being translated.

The term "siRNA" is intended to mean small interfering RNA used to performed RNAi.

DESCRIPTION OF THE PREFERRED EMBODIMENT

Figure 1:
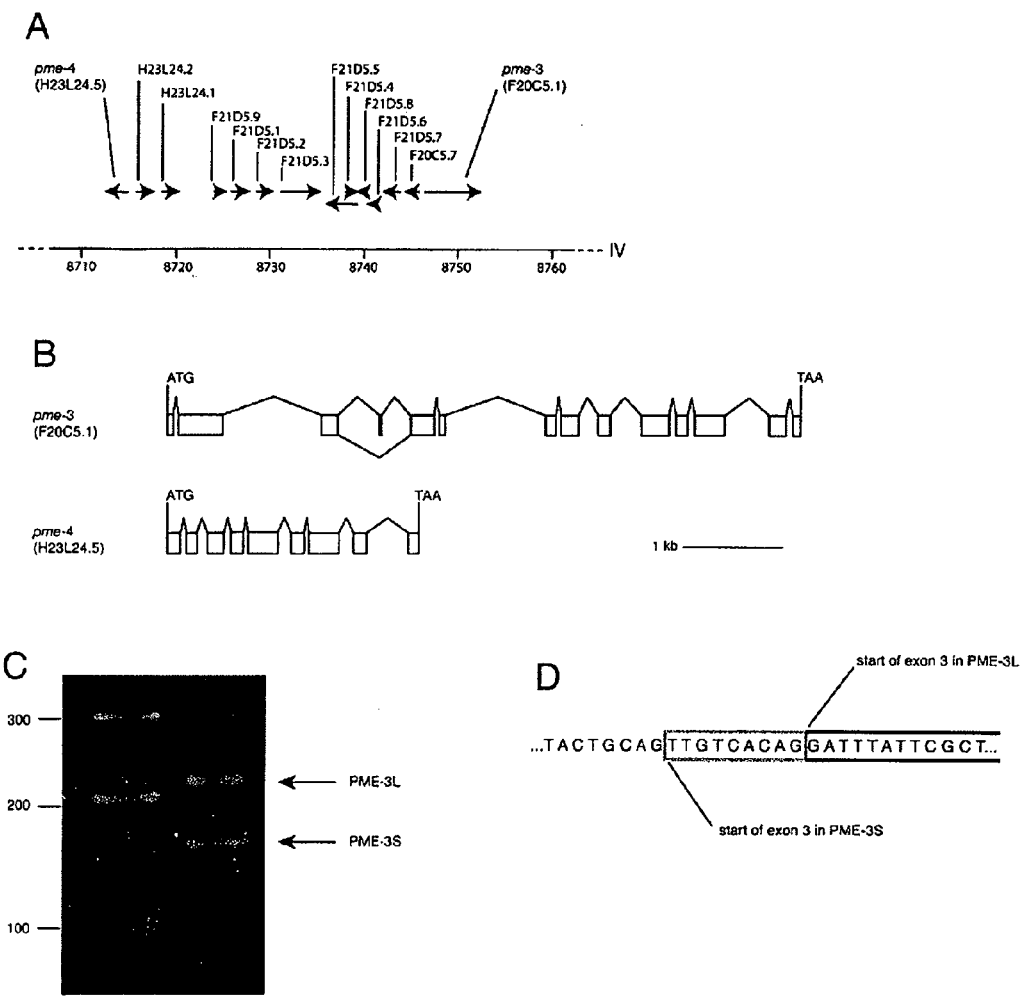
FIGS. 1A to 1D illustrate loci F20C5.1 and H23L24.5 encoding PARGs in *C. elegans;*

The present invention now will be described more fully hereinafter with reference to the accompanying drawings, in which preferred embodiments of the invention are shown. This invention, may, however, be embodied in many different forms and should not be construed as limited to the embodiments set forth herein; rather, these embodiments are provided so that this disclosure will be thorough and complete, and will fully convey the scope of the invention to those skilled in the art.

In accordance with the present invention, there is provided a method and a composition for inducing sensitization of human or animal cells that are targeted to be killed by a treatment with external elements. Among others, the cells can be conditionally sensitized by inhibiting or neutralizing the activity or the synthesis, such as at the level of the translation, transcription, or RNA maturation, factors that are necessary in maintaining the chromosome stability and integrity as well as in genotoxic recovery.

According to the present invention, the in vivo sensitization of target human or animal cells is performed by the inhibition or neutralization of the proteins pertaining to the PARP and PARG polypeptides, that are poly(ADP-ribose) metabolism enzyme (PME) polypeptide factors. Particularly, there are 6 different PMEs that can be targeted to carry out the method of the invention, pme-1, pme-2, pme-3L, pme-3S, pme-4 and pme-5, having respectively the nucleic acid sequences SEQ ID NO:1 to 6, and the corresponding amino acid PME-1, PME-2, PME-3L, PME-3S, PME-4, and PME-5, having respectively sequences SEQ ID NO:7 to 12.

The metabolism of poly(ADP-ribose) and high turnover rate after DNA-damages support a physiological role for PARG in DNA damage response and repair.

Particularly, PME-1 and PME-2 pertain to the PARPs group, PMEs-3 and 4 to the group of PARGs, and PME-5 is a member of the family of tankyrases. The effects of such an inhibition, resulting in sensitization, can lead to the impeachment of a variety of physiological events, such as chromatin decondensation, DNA replication, DNA repair, gene expression, malignant transformation, cellular differentiation, and apoptosis.

Inhibition or neutralization of one of the PMEs can be performed by treatment of different inhibitors known in the art having an activity directly or indirectly on PARP or PARG. For example, compounds for inhibiting PARG are discussed in Tanuma et al., JP 042-75223-A2; Tanuma et al., JP 042-75296-A2; Tanuma, JP 032-05402-A2; Tanuma, JP 04-013684-A2; Slama et al., J. Med. Chem. 38: 389–393 (1995); Slama et al., J. Med. Chem. 38: 4332–4336 (1995); Maruta et al., Biochemistry 30: 5907–5912 (1991); Aoki et al., Biochim. Biophys. Acta 1158: 251–256 (1993); Aoki et al., Biochem. Biophys. Res. Comm. 210: 329–337 (1995); Tsai et al., Biochemistry Intl. 24: 889–897 (1991); and Concha et al., Biochemistry Intl. 24: 889–897 (1991). All the inhibitors described in these references, incorporated herein by references, can be used to sensitize target cells to external elements.

The use of the PARG inhibitor tannic acid is described in Uchiumi et al., Biochem. Biophys. Res. Comm. 220: 411–417 (1996). Still another use for PARP inhibitors is described in Jianren Mao et al., 72: 355–366 (1997), also incorporated herein by reference.

A large number of known PARP inhibitors have been described in Banasik et al., "Specific Inhibitors of Poly (ADP-Ribose) Synthetase and Mono(ADP-Ribosyl)-Transferase", J. Biol. Chem., 267:3, 1569–75 (1992), and in Banasik et al., Molec. Cell. Biochem., 138: 185–97 (1994). Several PARG inhibitors have been described in Tavassoli et al., 827: 228–234 (1985). All references cited herein are incorporated by reference.

Alternatively, the inhibition or neutralization can be performed by submitting the target cells to transcription or translation inhibition. Among new methods that can be used, post-transcriptional gene silencing by double-stranded (ds) RNA is mentioned. In diverse organisms, double-stranded RNAs have been shown to inhibit gene expression in a sequence-specific manner. This biological process is currently termed RNA interference, or RNAi RNAi is a potent method, requiring only a few molecules of dsRNA, or siRNA, per cell to silence expression. It is known in the art that not only can silencing spread from the digestive tract to the remainder of the organism, but the effect can also be transmitted through the germ line for several generations.

According to one embodiment of the present invention, killing of cells sensitized by inhibition of a PME, can be performed in different manners, but preferentially it is done by radiation treatment. When submitting sensitized cells to gamma rays, a high lethal effect is obtained as compared to non sensitized cell also irradiated with gamma rays.

The present invention will be more readily understood by referring to the following examples which are given to illustrate the invention rather than to limit its scope.

EXAMPLE I

Inactivation of PARG in *C. elegans* Prevents Embryonic Survival After Gamma-irradiation Materials and Methods

*C. elegans* Strains

N2 worms (Bristol strain) were provided by the CGC (St-Paul, Minn.) and strain VC130 pme-3(gk120) was kindly provided by The *C. elegans* Gene Knockout Consortium. The strain VC130 was backcrossed 4 times to the wild-type worm. Deletion mutation was followed by PCR genotyping throughout the process.

*C. elegans* Culture and Extracts

Worms were handled and cultured as described (Gagnon et al., 2002, Biocem. J. 368: 263–271). Animals were grown at 20° C. on agar plates seeded with *E. coli* strain OP50. Liquid cultures were carried out in S basal medium supplemented with 5 g of *E. coli* strain NA22.

The worm extract was carried out as follows: Freshly washed worms (5 mL) were resuspended in 10 mL extraction buffer (50 mM KPO$_4$, pH 7.5, 50 mM KCl, 10 mM β-mercaptoethanol, 0.1% Triton X-100™) and passed twice at 8,000 psi in a French Pressure Cell (SLM-AMINCO®, Rochester, N.Y.) maintained at 4° C. The extract was centrifuged for 10 min at 1000×g at 4° C. The protein concentration of the supernatants (10.19 mg/ml for N2 and 6.7 mg/ml for pme-3(gk120) was determined according to Bradford.

Staged Worm Culture

Worms from a 1-liter culture were cleaned by sucrose flotation and the resulting pellet was treated with 40 µL of a hypochlorite alkaline solution (143 mM NaOH, 1.4% (w/v) sodium hypochlorite) for about 5 min with vortexing every minute. The mixture was then passed twice through a 21G needle. Eggs were quickly centrifuged and washed three times with 50 mL M9 buffer, transferred to 1 L S medium (without food) and allowed to hatch overnight with shaking at 250 rpm at 20° C. The L1 larva were supplemented with strain NA22 bacteria and collected 2 h later by centrifugation at 300×g. L2, L3, and L4 larva were collected after 12, 24, 36 h, respectively, and young adults, after 48 h. Each worm pellet was flash frozen in liquid nitrogen and stored at −75° C.

PCR Amplification of the 5'-Terminal Regions

To determine the trans-splicing nature of PME-3 and PME-4 Likewise, PCR amplifications for PME-4 messengers were done using SL1, SL2 and TATGGATCCATGGATCATGAAAACTTAATGAAGT (SEQ ID NO:13) as forward primers. The pme-4 gene-specific reverse primer was GTTGAGACACCCCTGTTTCC (SEQ ID NO:14). messengers, as well as their true 5'-end, PCR was performed on an oligo(dT)-primed cDNA library made from poly(A)$^+$ RNA from mixed-stage worm culture. PCR amplifications were done using SL1 primer (GTTTAATTAC-CCAAGTTTGAG SEQ ID NO:15), SL2 primer (GGTTT-TAACCCAGTTACTCAAG SEQ ID NO:16) or a gene-specific primer (TGTGGATCCATGAGCAAGAAGTTTATCGAAC SEQ ID NO:17) as forward primers and a gene-specific reverse primer (GACTGCGAGGAGACAAATACGTCACG SEQ ID NO:18). The PCR was a "two-step" type amplification: first, a denaturing step at 94° C. for 60 sec; second, a two-step sequence of 94° C. for 10 sec followed immediately by a step at 55° C. for 10 sec repeated 25 times and a final step at 72° C. for 5 min. PCR products generated by this method were excised from agarose gels and sequenced using automated sequencing.

Determination of Alternatively-spliced Isoform mRNAs

PCR amplification was used to show that exon 4 or pme-3 was alternatively spliced. The forward primer used was AGACACTACAACTCAACTGG (SEQ ID NO:19) and the reverse primer TGACAGGAAACTTGAACTGG )SEQ ID NO:20). The PCR conditions were the same as the amplification of the 5'-terminal regions. Amplicons were analysed on 0.8% agarose gel.

Cloning of cDNAs Encoding *C. elegans* PARGs

A BLAST search of the *C. elegans* EST database (Dr Yuji Kohara, Genome Biology Laboratory, National Institute of Genetics, Mishima, Japan) using the bovine PARG amino acids sequence (accession number U78975) located a clone yk356f1 encoding a partial cDNA of a putative PARG orthologue that we named poly(ADP-ribose) metabolism enzyme 3 (pme-3). The phagemid yk356f1 was excised and circularized using a standard method and the resulting plasmid was named pYK356f1. The primary nucleotide sequence of the insert of pYK356f1 was confirmed by automated sequencing. In order to obtain a full-length pme-3 cDNA, the missing 5'-end portion of the partial cDNA was amplified by PCR from an oligo(dT)-primed cDNA library made from poly(A)$^+$ RNA from mixed-stage worm culture. Forward primer was TTGTCCATGGGTACC ATGAGCAAGAAGTTTATCGAAC (SEQ ID NO:21) (initiation codon underlined) containing Nco I and Kpn I restriction sites, and reverse primer was TTGAAGTTCT-GCCCATTTTA. (SEQ ID NO:22) Both long (L) and short (S) pme-3 cDNA isoforms were selected by this amplification. The 1776 and 1827 nucleotides fragment amplified contained a unique PflMI site at position 1486. Once cleaved by PflMI restriction endonucleases, the fragments were ligated to the partial PME-3 cDNA in pYK356f1which was cleaved by Sma I and PflMI. Screening of bacterial colonies showed that the two PME-3 cDNA isoforms, L and S, were successfully cloned into pBluescript vector. The constructs were respectively named pBS-PME-3L and pBS-PME-3S. The PME-3L full-length cDNAs was then placed into Kpn I-Sal I digested pQE-30 expression vector after digestion with Kpn I-Xho 1. The construct was sequenced at the junctions with the pQE vector by automated DNA sequencing and named pQE-PME-3L.

The pme-4 cDNA was amplified by PCR from an oligo (dT)-primed cDNA library made from poly(A)$^+$ RNA from mixed-stage worm culture. The forward primer was TATG-GATCCATGGATCATGAAAACTTAATGAAGT (SEQ ID NO:23) (start codon underlined) and contained the BamHI restriction site. The reverse primer was TGTAAGCTTTGCTTTGGTGGAATTGA (SEQ ID NO:24) and contained the HindIII restriction site. The 1 495 bp amplicon was gel-purified, digested with appropriate restriction enzymes, and ligated into pET23a vector (Novagen, Madison Wis.). The resulting construct was named pET23a-PME-4 and its primary nucleotide sequence was determined by automated sequencing.

Duplex-PCR and Genotyping

In order to confirm the uniqueness of the gk120 mutation, pme-3(gk120) worms were backcrossed to wild-type worms. The process involves the production of heterozygous worms pme-3(gk120)/+ as intermediate and homozygous pme-3(gk120)/pme-3(gk120) as final step. Wild-type, heterozygous and homozygous worms were genotyped using a duplex PCR method. Two forward primers were used: ATTTTGACAAGGCGAGAGGA (SEQ ID NO:25) and CAGGCCATTTTTTGAGCCGT (SEQ ID NO:26) and one reverse TCTGGGTCAAATTCCCACAT (SEQ ID NO:27). The first forward primer is located at the 5'-end of the deletion and the second forward primer is located in the deletion. Therefore, the second forward primer together with the reverse primer (located at the 3'-end of the deletion), detects the wild-type allele (390 bp). The first forward primer together with the reverse primer detects the deletion (541 bp). The PCR was as follows: a single worm was placed in 10 µl lysis buffer (50 mM KCl, 10 mM Tris-HCl, pH 8.2, 2.5 mM MgCl$_2$, 0.45% NP-40, 0.45% Tween-20™, 100 μg/ml proteinase K) and covered with 10 μl mineral oil. Temperature was set at 60° C. for 1 h followed by steps at 95° C. for 15 min and 15° C. for 15 min. PCR was performed with 10 pmoles of each primer and started at 94° C. for 30 sec. The following 30 cycles used a 92° C. denaturation step for 10 sec, a 55° C. annealing step for 10 sec and a 72° C. elongation step for 10 sec. Heterozygous worms yield two bands: one at 390 bp for the wild-type chromosome and one at 541 bp for the gk120 allele. The homozygous worm yields only one band at 541 bp and wild-type worms a band at 390 bp.

RNA Interference

We obtained pme-3 and pme-4 dsRNA-synthesizing bacteria from MRC geneservice (Cambridge, UK). The expression of sense and antisense RNA was induced in HT115 (DE3) bacteria by addition of 0.4 mM IPTG, for 4 h at 37° C. RNAi was performed by feeding synchronized L4 larvae with the induced bacterial culture for 4 days (Kamath et al., 2000, Genome Biol. 2). L4 from the progeny, still fed with this culture, were isolated and irradiated at 120 Gy for survival determination.

Bacterial Cultures and Extracts

Cultures of M15-pREP4 bacteria transformed with pQE-PME-3L, were grown overnight at saturation at 37° C. Fresh cultures (1000 ml) were started with 50-mL overnight cultures and grown at 37° C. at OD$_{600\,nm}$ 0.600. Cultures were then induced with 1 mM isopropyl-1-thio-β-d-galactopyranoside (IPTG) at 37° C. for 2.5 h. M15-pREP4 bacteria transformed with vector alone were also treated with 1 mM IPTG at 37° C. for 2.5 h. Cultures were pelleted at 3000×g for 10 min at 4° C., resuspended in 10 ml extraction buffer (50 mM KPO$_4$, pH 7.5, 50 mM Kcl, 10 mM β-mercaptoethanol, 0.1% triton X-100) and passed twice at 16,000 psi in a French Pressure Cell (SLM-AMINCO®, Rochester, N.Y.) maintained at 4° C. Extracts were centrifuged for 10 min at 1000×g at 4° C. and protein concentration of supernatants were determined. Each supernatant (23.7 mg/ml for M15+pQE-30 and 22.2 mg/ml for pQE-PME-3L) were analyzed on SDS-PAGE and assayed for PARG activity.

Western Blot

Bacteria were grown and induced as above in 50 ml LB. Samples of 1.5 ml were taken from the culture before and after induction. They were centrifuged and pellets were dissolved in 400 μl sample buffer (50 mM Tris-Hcl, pH 8, 2% SDS, 10% glycerol, 5% v/v β-mercaptoethanol, 0.0015% bromphenol blue). Samples (10 μl) were loaded in adjacent wells on a 10% (w/v) acrylamide mini-gel containing 0.1% (w/v) SDS. After the electrophoresis, the polypeptides were electrophoretically transferred to nitrocellulose (1 h, 4° C., 100 volts). The filter was blocked with PBSTM (0.1% (v/v) Tween-20, 5% (w/v) powdered milk in 137 mM NaCl, 2.7 mM KCl, 1.5 mM KH$_2$PO$_4$, 8 mM Na$_2$HPO$_4$, pH 7.4) for 1 h at room temperature, and incubated for 18 h at 4° C. with a mouse anti-HIS antibody (anti-polyhistidine clone His-1, Sigma. Chemical) diluted 1:1000 in fresh PBSTM. Following three washes with PBSTM, the membrane was incubated for 30 min with peroxidase-coupled anti-mouse Ig diluted 1:10 000 in fresh PBSTM. After three additional washes with PBSTM and one in water, a bound antibody was detected using a chemiluminescence kit (Renaissance, DuPont Chemical Co., Boston, Mass.).

Mass Spectrometry

Protein samples from non-induced and induced M15-pREP4 bacteria transformed with pQE-PME-3L were run on a SDS-PAGE and stained with Coomassie. After visual inspection, a band appearing only in the induced sample was excised from the polyacrylamide gel and digested with trypsin. The tryptic digest was subsequently analyzed by LC/MS/MS mass spectrometry on a LCQ Deca XP (Thermo Finnigan) equipped with an electronanospray ion source.

Determination of PARG Activity in Worm and Bacterial Extracts

PARG activity was determined according to Ménard et al (1987, Biochem. Cel Biol. 65: 668–673). Ten μl of worm or bacterial extracts were assayed for 24 h at 37° C. in the presence of $^{32}$P-poly(ADP-ribose) followed by a thin layer chromatography. Radiolabeled ADP-ribose units released from ADP-ribose polymers were quantified directly on the TLC using an Instant Imager Electronic Autoradiography device (Canberra-Packard). One unit of PARG is defined as the amount of enzyme required to liberate 1 nmol of ADP-ribose per min at 37° C. under assay conditions (Menard and Poirier, 1987, Biochem. Cell Biol. 65: 668–673). Radiographic X-OMAT film was exposed to the TLC plate and placed at −80° C. for 24 h.

Irradiation and Survival Determination

L4 worms were irradiated at 120 Gy (Hematology and Oncology Services, Hôtel-Dieu de Québec), then placed individually on fresh plates and allowed to lay eggs for 44 hours. After this period of time, the hermaphrodites were removed from the plates. Embryos laid but not hatched after a period of 48 h were counted as dead individual (Gartner et al., 2000, Mol. Cell 5: 435–43).

Computer Analysis

The deduced amino acid sequences of bovine PARG (accession number U78975) was used to search the C. elegans Sequence database at the Sanger Centre and the C. elegans EST database (Dr Yuji Kohara, Genome Biology Laboratory, National Institute of Genetics, Mishima, Japan). Database searches were done using the TBLASTN of the BLAST program. Analyses of sequence data and sequence comparisons were performed using the CLUSTALW program of the Lasergene package (DNASTAR, Inc., Madison, Wis.).

Results

Cloning of the full-length pme-3 and pme-4 cDNA in C. elegans—A search of the C. elegans protein data bank with deduced amino acid sequence of the bovine PARG (accession number U78975) revealed two loci (F20C5.1 and H23L24.5 (pme-4, GenBank accession number AF548468)) that encode putative PARGs. Localization of pme-3 (locus F20C5.1) and pme-4 (locus H23L24.5) on chromosome IV. (A) The loci are approximately 35 kbp apart with 12 putative genes (arrows) in between. Numbers represent the nucleotide position (in thousands) on chromosome IV. (B) Gene organization of pme-3 and pme-4. The pme-3 gene spans over 6.3 kb and is composed of 13 exons (open boxes), pme-4 spans over 2.4 kb and is composed of 9 exons. Start codon (ATG) and stop codon (TAA) are indicated. (C) pme-3 is alternatively spliced. PCR amplification using a set of primers located on exon 3 and exon 5 shows the two PME-3 isoforms: PME-3S and PME-3L. (D) Details of nucleotide sequence of exon 3 of PME-3S: 9 nucleotides are present in PME-3S and absent in PME-3L. The two loci are 31 225 nucleotides apart, on chromosome IV. The present study on the gene pme-3, located atlocus F20C5.1 which spans over 6 304 nucleotides, and contains 13 exons (FIG. 1A). During the course of cloning the cDNA of pme-3, we observed a shorter spliced isoform of PME-3 (FIG. 1B), which we denoted PME-3S (GenBank™ accession number AY185494, protein id AAO26317). The full-length cDNA sequence of PME-3L (GenBank™ accession number AY185493, protein id AAO26316) contains 2 666 nucleotides, including a 5'-untranslated region consisting of the splice leader-1 (GGTTTAATTACCCAAGTTTGAG, nucleotides 1 to 22 (SEQ ID NO:28)), a untranslated genomic sequence (GCAGAAATAGACTTTCACAAAACACATC-GACACATCGACACTTCGA nucleotides 23 to 60 (SEQ ID NO:29)), an open reading frame of 2 346 nucleotides and a 3'-untranslated region of 260 nucleotides including a poly (A)$^+$ tail. The PME-3S cDNA is essentially the same except for an additional 9 nucleotides at the beginning of exon 3 and the lack of exon 4 (FIGS. 1C and D).

The predicted PME-3L protein has a calculated molecular mass of 89,292 Da with an estimated pI of 4.9 (charge at pH 7 is −34). The PME-3S protein has a predicted mass of 87,450 Da and its calculated pI is 5.0 (charge at pH 7 is −31). The PME-3L is thus smaller than PARGs found in higher eukaryotes (FIG. 2A). A PSORT II analysis predicts the localization of PME-3L to be in the cytoplasm like its bovine counterpart. (A) Structural organization of PARGs from different species (huPARG, human, GenBank accession number AAB61614; boPARG, bovine, GenBank accession number AAB53370; raPARG, rat, GenBank accession number BAA87901; moPARG, mouse, GenBank accession number AAC28735; drPARG, *Drosophila melanogaster*, GenBank accession number AAC28735; atPARG1, *Arabidopsis thaliana*, GenBank accession number AAK72256; atPARG2, *Arabidopsis thaliana*, GenBank accession number NP850175; PME-3L, *C. elegans*, GenBank accession number AAO26316; PME-4, *C. elegans*, GenBank accession number AAN40699; agPARG, *Anopheles gambiae*, GenBank accession number EAA06681). Numbers at left and right refer to amino acid position. The photoderivatized (PD) region (black box) is localized in the C-terminal portion of the enzymes. Number inside the black boxes indicates percent similarity to huPARG PD region. (B) Alignment of the deduced amino acid sequences the PD region of PARGs. PD region contains critical amino acids for enzymatic activity for tyrosine 796 (*) in boPARG. This residue is conserved in PME-3 and PME-4 as well as in PARG of other species. Numbers indicate amino acid position. Amino acids that are identical are boxed in black. Conserved substitutions are indicated in grey.

Its structural similarities to human and other eukaryotic PARGs (FIG. 2A) is essentially localized in a small region, the photoderivatized motif (Koh D W, et al., Biochemistry 2003 May 6;42(17): 4855–4863), in the C-terminal part (FIGS. 2A and B). This motif is believed to contain essential amino acids residues responsible for PARG activity. The overall identity of PME-3 compared with human PARG is only 18%, but rises to 42% when both catalytic motifs PD motifs are compared.

The cloned cDNA of pme-4 (SEQ ID NO:5) (GenBank accession number AF548468) has a length of 1 523 nucleotides consisting of a SL1 sequence at the 5'-end followed by a 43 nucleotides sequence of untranslated genomic DNA and an open reading frame (ORF) of 1458 bp. The primers used for the amplification of pme-4 cDNA were designed according to a GeneFinder® prediction. Therefore, there is a slight possibility that the 3'-end of this cDNA may not represent the natural end of pme-4 mRNA. The PME-4 protein (SEQ ID NO:11) has a calculated molecular mass of 58,480 Da with an estimated pI of 7.1 (charge at pH 7 is 0.266). PME-4 is the smallest of *C. elegans* PARGs (FIG. 2A). PME-4 has an overall identity of 22% with human PARG and, if just PD motifs are compared, homology is 40%. It is thus likely that both PME-3 and PME-4 are able to degrade pADPr polymers.

Structural Analysis of pme-3 mRNA

Figure 3:
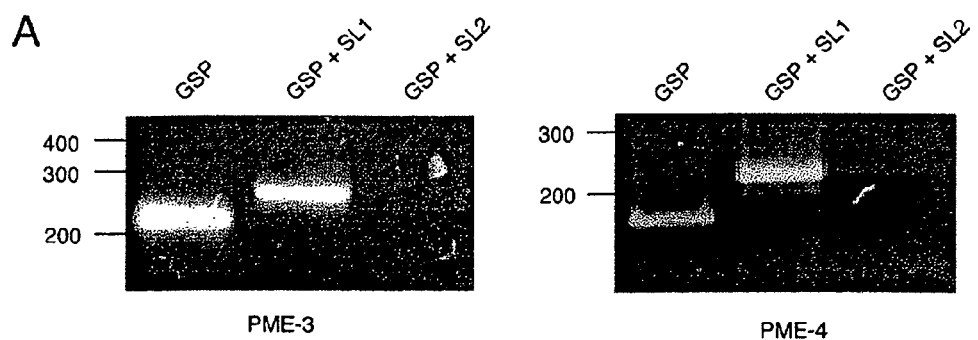
FIGS. 3A to 3C illustrate the expression of pme-3 and pme-4 in *C. elegans;*
Figure 3:
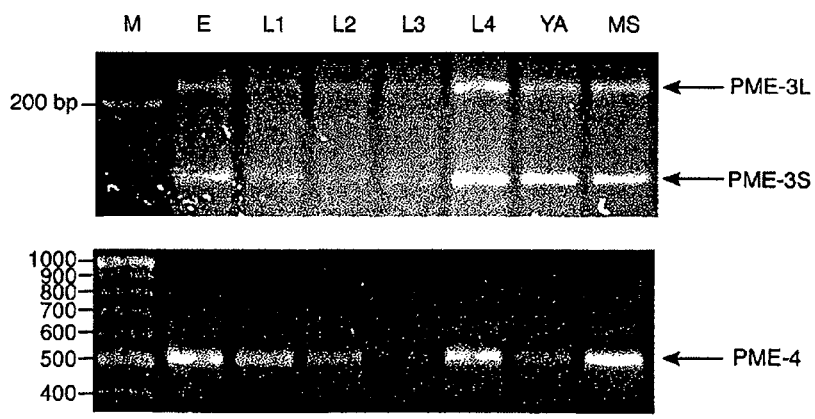

The 5'-ends of PME-3 RNA was analyzed by RT-PCR using splice leader-1 (SL-1) or splice leader-2 (SL-2) as forward primer and a gene-specific primer as reverse primer (FIG. 3A). We show that PME-3 mRNA has the SL-1 sequence in its 5'-end (FIGS. 3A and B). It also confirms the sequence of the real 5'-end of the messenger. This suggests that pme-3 is most probably not part of an operon and that its expression should not be polycistronic in nature. (3A) RT-PCR amplification of 5'-end of PME-3 and PME-4 transcripts. A pair of gene-specific primers (GSPs) for PME-3 and PME-4 was selected to yield a 206 bp and a 175 bp PCR products respectively. A second and a third PCR amplification using SL-1 and SL-2 primers as forward primers and the same reverse GSP for PME-3 and PME-4 yielded a 257 bp product for SL1/PME-3 and a 231 bp PCR product for PME-4. (3B) Sequence determination of PCR products SL1/PME-3 and SL1/PME-4. Capital letters indicate splice leader sequences, bold letters indicate genomic UTR, and lowercase indicates translated sequences. (3C) Qualitative RT-PCR analysis of pme-3 and pme-4 expression in each developmental stage of the worm. Both PME-3S (153 bp band) and PME-3L (213 bp band), and PME-4 (513 bp band) are expressed during the life cycle of the worm. Marker (M), embryo (E), larva L1, L2, L3 and L4 are indicated as well as young adult (YA) and mixed stages (MS). The markers (M) are shown at left.

Developmental Expression of pme-3

Figure 4:
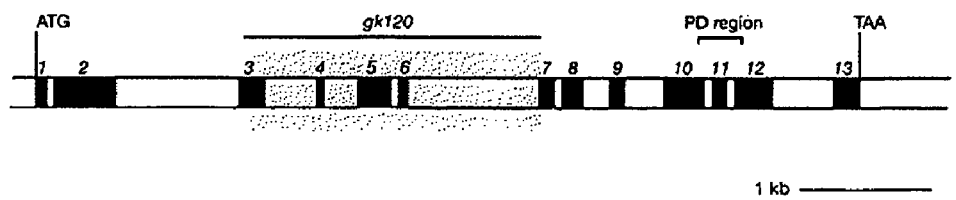
FIGS. 4A to 4C illustrate that the allele gk120 is a deletion mutation in the gene pme-3.
Figure 4:
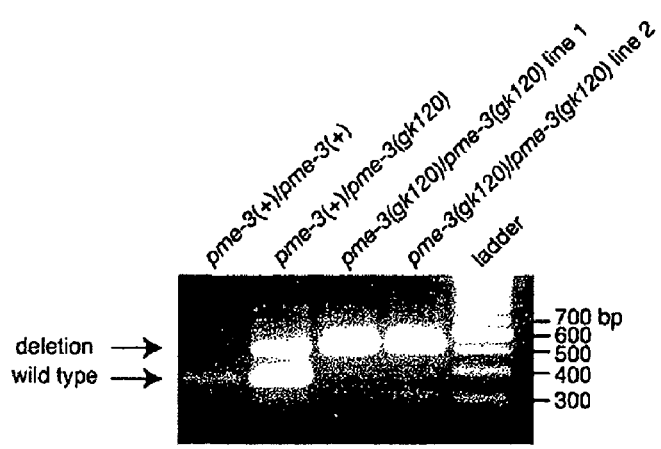

RT-PCR of PME-3 mRNA expression is shown (FIG. 3C). Total RNAs from animals of all developmental stages were tested with the same set of primers used to show the pme-3 alternatively spliced isoforms. Both forms, PME-3L (SEQ ID NO:9) and PME-3S (SEQ ID NO:10), were detected in all developmental stages, suggesting that both forms are needed during development. FIG. 4 shows: (A) Schematic representation of the genomic portion housing the pme-3 gene. The 2,304 nucleotides deletion is shown in grey. The PD region is encoded in part by exon 10, exon 11 and exon 12. Black boxes are exons. ATG, start codon. TAA, stop codon. (B) Nucleotidic sequence showing the deletion. Numbers refer to the nucleotide position in genomic DNA where the A of the start codon is 1. (C) Duplex PCR-based genotyping of wild type pme-3(+)/pme-3(+) worms, heterozygous pme-3(+)/pme-3(gk120) worms, and homozygous pme-3(gk120)/pme-3(gk120) worms (See Material and Methods for details). The homozygous pme-3(gk120) worms were used for the rest of the study.

pme-3(gk120) Worms

Figure 5:
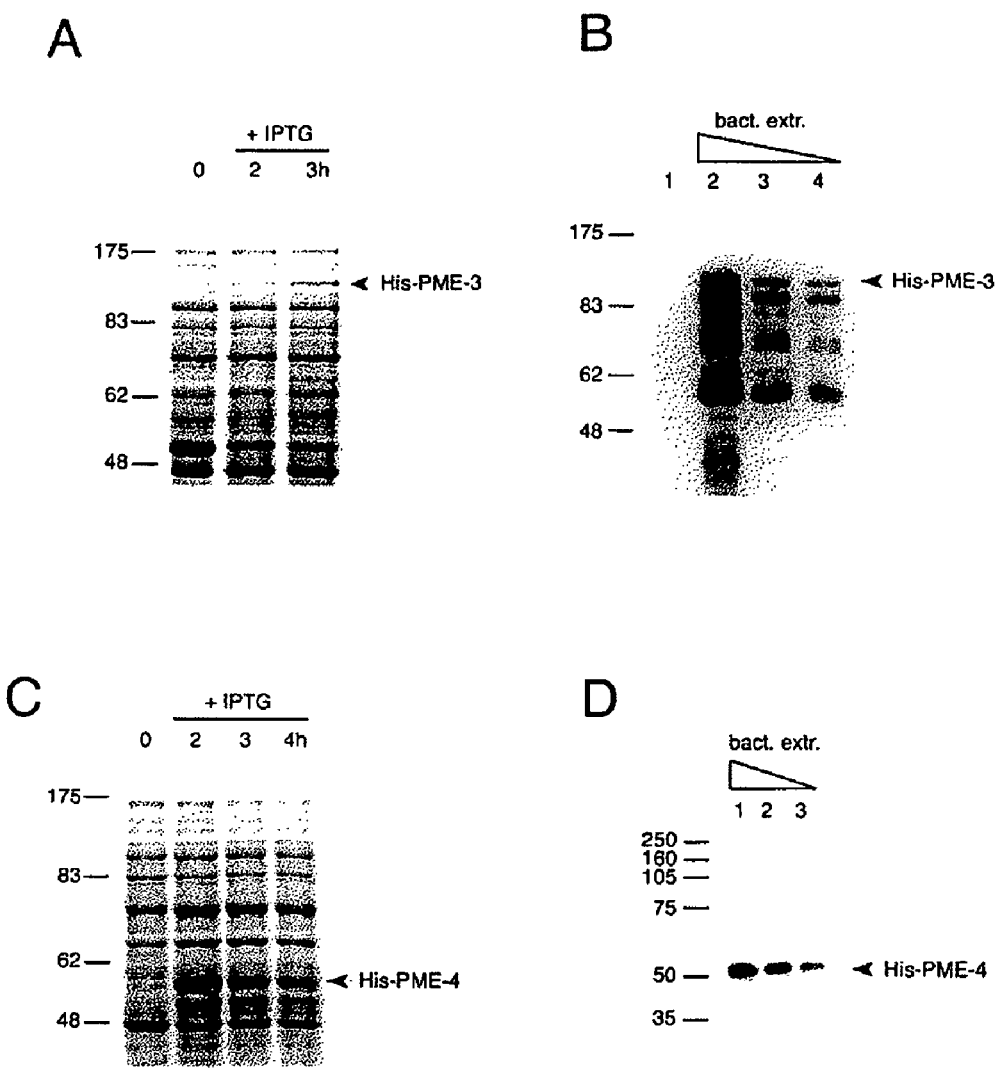
FIGS. 5A to 5D illustrated the bacterial expression of His-PME-3 and His-PME-4 recombinant enzymes.

The allele gk120 is a loss-of-function mutation characterized by a deletion in the gene pme-3 (FIG. 5). (5A) M15 bacteria were transformed with pQE-PME-3L and induced for 2 and 3 h with IPTG. Samples of 1.5 ml bacterial cultures were centrifuged and pellets dissolved in 400 μl sample buffer. Total extract (10 μl) were then analyzed on SDS-PAGE and stained with Coomassie. Recombinant His-PME-3L appears at 139 kDa. (5B) Total extract (10 μl not diluted (ND) and diluted 1/10 and 1/20) of bacteria expressing His-PME-3L for 2 h were analyzed by western blot using an anti-His antibody. UI, noninduced. (5C) BL21 bacteria transformed with pET23a-PME-4 were induced with IPTG for 4 h with IPTG. Samples of 1.5 mL bacterial cultures were centrifuged and pellets dissolved in 450 μL sample buffer. Volume of 10 μL of total extract were then analyzed on SDS-PAGE and stained with Coomassie. The arrow points to a band corresponding to His-PME-4. (5D) Total extract (10 μL diluted 1/20, 1/40, and 1/80) of bacteria expressing His-PME-4 for 4 h were analyzed by western blot using an anti-His antibody. A control (C) consisting of BL21 bacteria transformed with pET-23a was induced for 4 h with IPTG. Extract was diluted 1/10 and 10 μL were analyzed on western blot. Numbers at left of panels indicate molecular weight in kDa. The deletion starts 1,363 nucleotide downstream from the start codon and runs for 2,304 nucleotides. The exons 3 to 7 are partially or totally removed. We backcrossed gk120 to wild-type animals in order to remove any other mutations that may have been introduced during mutagenesis. The backcross yielded heterozygous and homozygous animals (FIG. 5B). The animals used in this study were homozygous for the gk120 allele. Hermaphrodites with the gk120 allele have progenies with a higher male-to-hermaphrodite ratio compared with the wild-type worms (Table 1). In fact, they have 35 times more males than the wild-type.

TABLE 1 pme-3 (gk120) worms display a him phenotype

| Strain | n | Hermaphrodite | male | Ratio M/H |
|---|---|---|---|---|
| N2 | 9 | 1687 | 1 | 0.06 |
| pme-3 (gk120) | 9 | 1969 | 41 | 2.08 |

Poly(ADP-ribose) Glycohydrolase Activity in *C. elegans* Worm Extract

Figure 6:
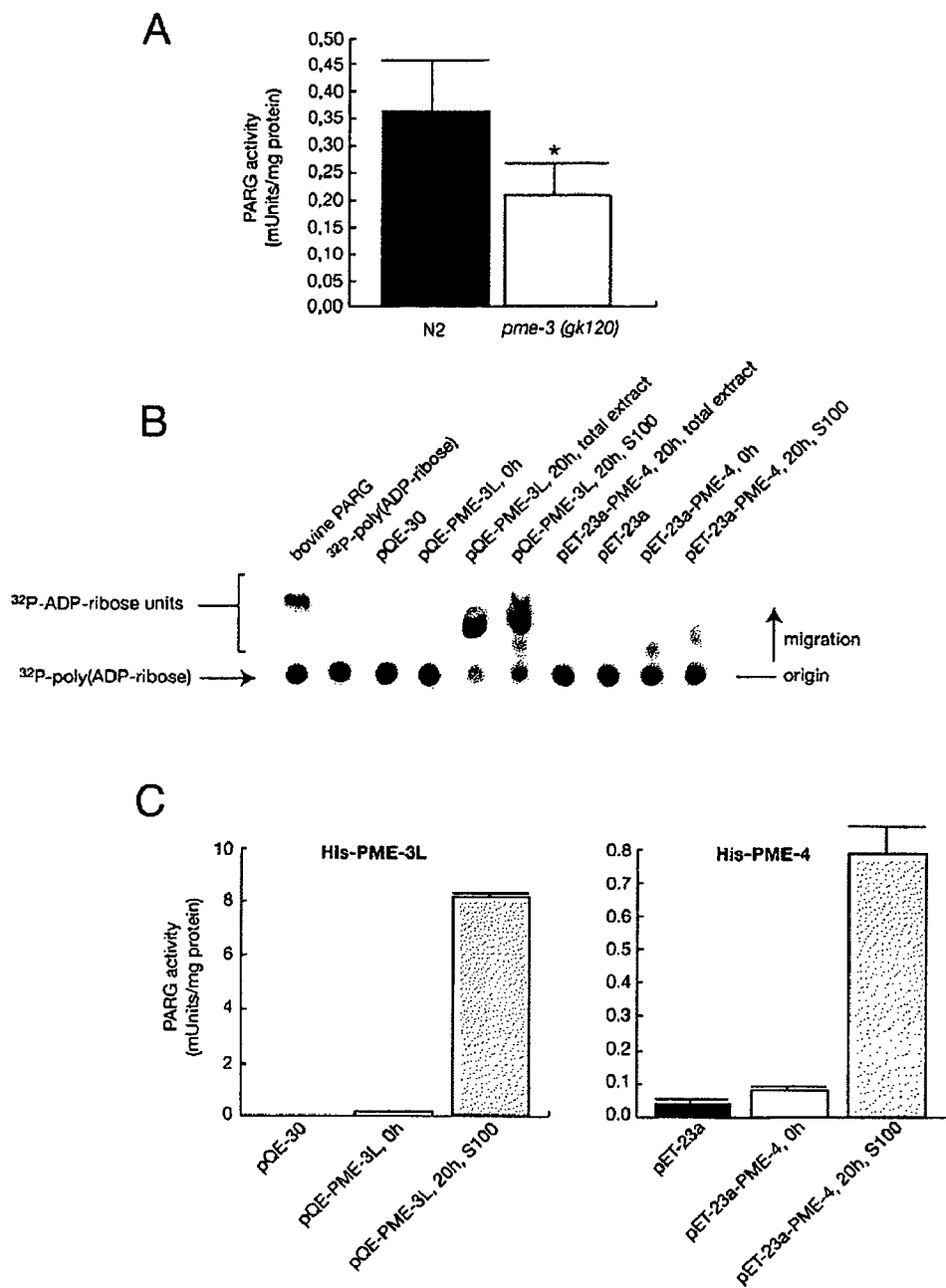
FIGS. 6A to 6C illustrate the PARG activity detected in worm extract and in bacterial extract expressing recombinant PME-3 and PME-4.

We conducted quantitative PARG assays on *C. elegans* to verify that the structurally associated PARG in the worm have indeed PARG activity. To do so, wild-type and pme-3(gk120) worm extracts were made from fresh mixed-stage cultures. Total extracts were then tested for PARG activity using the thin layer chromatography assay that measures release of $^{32}$P-ADP-ribose from $^{32}$P-poly(ADP-ribose) (Menard and Poirier, 1987, Biochem. Cell Biol. 65: 668–673). PARG activity was detected in both extracts. Worms bearing the homozygous gk120 mutation in the pme-3 gene have approximately three times less PARG activity than wild-type (4.8 compares to 16.2 μUnits/mg) (FIG. 6A). This strongly suggests that PME-3 is a bona fide PARG in *C. elegans*. It also shows for the first time the presence of an endogenous activity of poly(ADP-ribose) glycohydrolase in the worm. FIG. 6A shows worm extracts (N2 wild-type and pme-3 (gk120)) were mixed with equal amount $^{32}$P-pADPr for 24 h at 37° C. and analyzed on TLC. Bar represents PARG activity based on the release of $^{32}$P-ADP-ribose units from $^{32}$P-ADP-ribose polymers. Determinations were done in triplicates 3 times from 3 different extracts. The asterisk (*) indicates a significant difference (P<0.0002). FIG. 6B is a representative PARG assay on TLC for. bacterially-expressed His-PME-3L and His-PME-4. Equal amount of purified $^{32}$P-pADPr (10 μl) were mix with 10 μL of the different samples. Volumes of 10 μL of the reaction mix were deposited at the origin and resolved on TLC. A positive control (bovine PARG) shows the separation of $^{32}$P-ADP-ribose units from undigested $^{32}$PpADPr A control consisting of $^{32}$P-pADPr alone shows the stability of the polymer at 37° C. for 24 h. Bacterial extracts transformed with vector alone (pQE-30 and pET-23a) or noninduced bacterial extracts (pQE-PME-3L, 0 h and pET-23a-PME-4, 0 h) do not contain PARG activity. Total bacterial extracts supernatant (S100) expressing His-PME-3L and His-PME-4 induced for 20 h display PARG activity. Variation in the migration pattern may be due to salt content. FIG. 6C is a quantitative determination of PARG activity in supernatant (S100) of bacterial extract transformed with vector alone (pQE-30 and pET-23a), uninduced (pQE-PME-3L, 0 h and pET-23a-PME-4, 0 h) or induced for 20 h at 4 C. (pQE-PME-3L, 20 h, S100 and pET-23a-PME-4, 20 h, S100).

Figure 7:
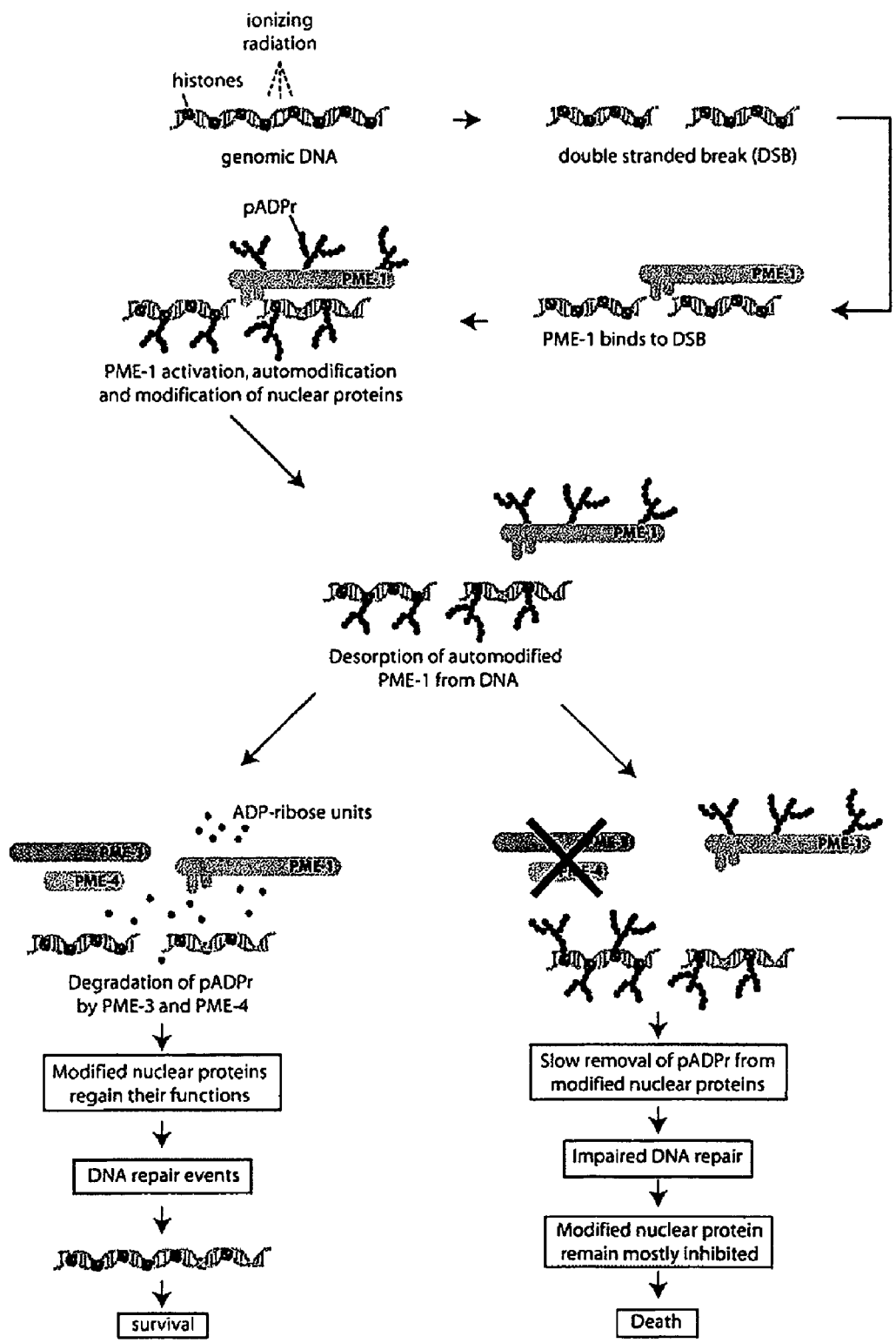
FIG. 7 shows a model of poly(ADP-ribose)-induced death.

FIG. 7 shows a model of poly(ADP-ribose)-induced death. Ionizing radiations generate double strand breaks (DSB) in genomic DNA. DSB may be detected by PME-1 (PARP-1 orthologue) through the zinc fingers and stimulate its activity. Poly(ADP-ribosyl)ation of PME-1 and surrounding nuclear proteins, including histones, take place. Automodified PME-1 is turned off and desorbed from DNA. Simultaneously, PME-3 and PME-4 (*C. elegans* PARGs) are activated when pADPr polymers reach a critical concentration. Polymers are rapidly degraded and modified proteins regain their original functions, allowing DNA repair and ultimately survival to occur. In absence of PME-3 and PME-4, pADPr polymers are, at best, slowly removed, which impair DNA repair and other cellular processes leading to death.

Determination of PARG Activity in PME-3 and PME-4 Recombinant Protein

The full length pme-3L (SEQ ID NO:3) and pme-4 (SEQ ID NO:5) cDNAs were cloned in the pQE-30 and pET-23a bacterial expression vectors respectively. The resulting recombinant proteins are His-tagged proteins (FIG. 5) with predicted molecular weights of 91 256 Da for His-PME-3L (SEQ ID NO:9) and 57 890 Da for His-PME-4 (SEQ ID NO:11). Analysis of bacterial extracts expressing His-PME-3L showed that the recombinant protein unexpectedly migrates to a Mr of 138 kDa (FIG. 5A). Western blot using a monoclonal anti-His antibody showed that His-PME-3L is not expressed in bacteria transformed with vector alone, and His-PME-3L protein seems to migrate at a larger Mr than the one predicted (FIG. 5B). Mass spectrometry of proteins contained in the 138-kDa band revealed that His-PME-3L was the predominant protein. Degradation products were also detected and seemed to be a hallmark of recombinant PARG (Lin et al., 1997, J. Biol Chem., 272: 269–270). His-PME-4 was over-expressed at its expected Mr (FIG.

5C). A western blot shows that His-PME-4 is more stable than His-PME-3L, as no degradation products were detected (FIG. 5D).

Extract from bacteria transformed with construct pQE-PME-3L and pET-23a-PME-4 displayed PARG activity (FIGS. 6B and C). The activity is present in total extract as well as supernatants (S100) indicating that both proteins are at least partially soluble when expressed in bacteria. A control using the substrate $^{32}$P-pADPr and water alone (no protein sample) was introduced and showed that incubation for 24 h at 37° C. did not release $^{32}$P-ADP-ribose units. This suggests that, in our bacterial expression system, the release of $^{32}$P-ADP-ribose units depends upon the expression of recombinant His-PME-3L or His-PME-4. We noticed that the expression in bacteria grown at 22° C. yielded more PARG activity than an expression at 37° C. for the same length of time. Moreover, expression done at 4° C. for 16 h yielded more PARG activity for PME-4 than expression at 37° C. These data suggest that PARG enzyme molecule are unstable and may be toxic to the bacteria. It is interesting to note that, even with a similar rate of bacterial expression, His-PME-3L displayed almost 10 times more PARG activity compare to His-PME-4 (FIGS. 6B and C). This may suggest that PME-3L is in fact more active in the worm.

Gamma-irradiation and Embryonic Survival

Mammalian PARP-1 is known to detect breaks in DNA. PARP-1 then stimulates its activity and pADPr polymers are synthesized. PARG rapidly degrades the polymers into ADP-ribose units. To determine whether C. elegans PARGs play a role in DNA damage response, we treated pme-3(gk120) worms with 120 Gy of gamma rays. Survival of F1 progeny decreased to 39% from 71% for wild-type worms (Table 3). Survival decreased to 45% when using RNAi (Table 3). The differences in survival rates between deletion mutant and RNAi may be attributed to the incomplete knock-out effect of gene silencing. Knock-down of pme-4 expression using RNAi in wild-type animals decreased slightly the survival of F2 progeny to 67%. When pme-4 expression is knocked-down in a pme-3(gk120) background, the survival further decreased to 20% (Table 3). A similar effect is shown when worms are subjected to RNAi with pme-3 and pme-4 dsRNA (Table 3). Therefore, depletion of C. elegans PARGs enhances the sensitivity to ionizing radiation.

Figure 2:
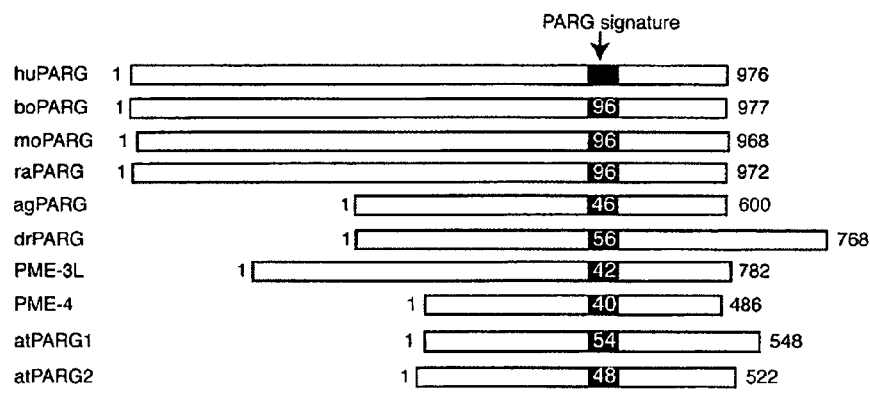
FIGS. 2A and 2B illustrate that PME-3 and PME-4 are structurally related to PARG found in other animals.
Figure 2:
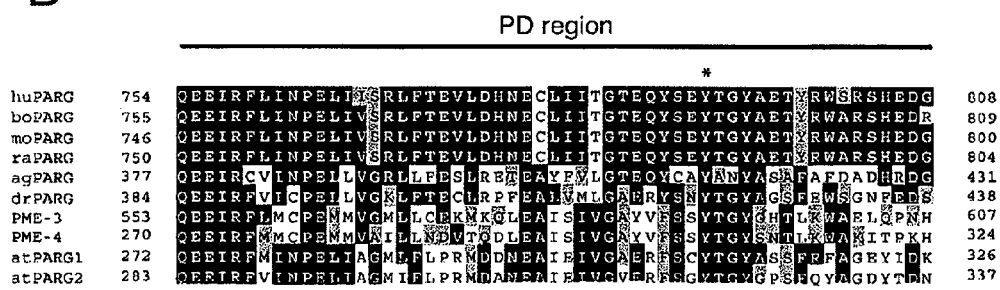

The gene pme-3 codes for a predicted protein that shares sequences similarity with the PD motif in the catalytically active C-terminal portion of PARGs from other organisms (FIG. 2). This gene and pme-4 would thus mediate the PARG activity detected in the worm (FIG. 6A). To support this hypothesis we showed that His-PME-3L and His-PME-4 proteins display PARG activity (FIG. 6B,C). Moreover, worms with the allele gk120 display half PARG activity than wild type animals. The residual PARG activity in gk120 worms may be provided by PME-4 and unknown enzyme able to digest pADPr polymers.

TABLE 2

Inactivation of pme-3 and pme-4 show significant decrease in survival after radiation-induced DNA damage

| | gamma radiation | | | | | | |
|---|---|---|---|---|---|---|---|
| | 0 Gy | | | | 120 Gy | | |
| Genotype | n | Laid | Hatched | Percent of survival | n | Laid | Hatched | Percent of survival |
| N2 | 4 | 218 | 217 | 99% | 6 | 157 | 111 | 71% |
| pme-3(gk120) | 4 | 1349 | 1252 | 93% | 6 | 209 | 82 | 39% |
| pme-3(RNAi) | 5 | 460 | 459 | 99.8% | 10 | 291 | 160 | 45.0% |
| pme-4(RNAi) | 5 | 539 | 538 | 99.8% | 10 | 586 | 335 | 57.2% |
| pme-3(gk120)pme-4(RNAi) | 7 | 370 | 365 | 99% | 15 | 1671 | 327 | 20% |
| pme-3(RNAi)pme-4(RNAi) | 10 | 962 | 959 | 99.7% | 15 | 530 | 148 | 27.9% |

The general anatomy and the behavior of gk120 worms are almost identical to wild type worms except for two significant aspects. First, in normal condition of culture, gk120 display a him (high incidence of male) phenotype. Second, in the presence of a genotoxic stress such as gamma-irradiation, gk120 worms have a decreased capacity of survival. Both of these phenotypes are characteristics of altered DNA-repair as well as chromosomal segregation mechanisms.

When pme-3(gk120) worms as well as pme-3(RNAi) and pme-4(RNAi) or both pme-3(RNAi)pme-4(RNAi) were tested for their capacity to survive genotoxic stress, survival was significantly below what wild type worms were able to achieve (Table 2). Therefore, pme-3 and pme-4 provide a protection against such aggression. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

I claim:

1. A method for killing human cells or animal cells comprising the steps of:
   a) inhibiting the expression of a polynucleotide encoding the polypeptide sequence of SEQ ID NO: 9 in human cells or animal cells thereby causing the sensitization of said cells;
   b) treating cells sensitized in step a) with a dose of a chemical entity or irradiation effective to kill said cells.

2. The method of claim 1 wherein said chemical entity is a PARP or a PARG inhibitor.

3. The method of claim 1 wherein said chemical entity is a PME inhibitor.

4. The method of claim 2 wherein said PARP inhibitor is selected from the group consisting of 3-aminobenzamide, 1,5-dihydroxyisoquinoline, and PJ-34.

5. The method of claim 2 wherein said PARG inhibitor is selected from the group consisting of gallotannin, nobotanin B, 8-(aminohexyl)amino-ADP-HPD, siRNA-PARG, and siRNA-PME.

6. The method of claim 1 wherein said irradiation is performed with gamma rays.

7. The method of claim 1 wherein step a) is performed by RNA interference.

* * * * *